US012565886B2

(12) United States Patent
Barrett et al.

(10) Patent No.: US 12,565,886 B2
(45) Date of Patent: Mar. 3, 2026

(54) SYSTEMS, DEVICES, AND METHODS RELATING TO A COOLED RADIOFREQUENCY TREATMENT PROCEDURE

(71) Applicant: AVENT, INC., Alpharetta, GA (US)

(72) Inventors: Jennifer J. Barrett, Alpharetta, GA (US); Lisa M. Mcgregor, Alpharetta, GA (US); Michael Douglas Brown, Alpharetta, GA (US)

(73) Assignee: AVENT, INC., Alpharetta, GA (US)

( * ) Notice: Subject to any disclaimer, the term of this patent is extended or adjusted under 35 U.S.C. 154(b) by 6 days.

(21) Appl. No.: 18/711,048

(22) PCT Filed: Nov. 18, 2022

(86) PCT No.: PCT/US2022/050389
§ 371 (c)(1),
(2) Date: May 16, 2024

(87) PCT Pub. No.: WO2023/091659
PCT Pub. Date: May 25, 2023

(65) Prior Publication Data
US 2024/0426292 A1    Dec. 26, 2024

Related U.S. Application Data

(60) Provisional application No. 63/281,241, filed on Nov. 19, 2021.

(51) Int. Cl.
*F04B 51/00* (2006.01)
*A61B 17/00* (2006.01)
(Continued)

(52) U.S. Cl.
CPC .............. *F04B 51/00* (2013.01); *A61B 18/12* (2013.01); *A61B 18/148* (2013.01); *F04B 43/12* (2013.01);
(Continued)

(58) Field of Classification Search
CPC ........... A61B 2018/00005; A61B 2018/00011; A61B 2018/00023; A61B 18/12–1492;
(Continued)

(56) References Cited

U.S. PATENT DOCUMENTS

| | | | | |
|---|---|---|---|---|
| 5,657,000 | A | * | 8/1997 | Ellingboe ............... F04B 49/06 |
| | | | | 417/63 |
| 8,882,755 | B2 | | 11/2014 | Leung et al. |

(Continued)

FOREIGN PATENT DOCUMENTS

| | | | | |
|---|---|---|---|---|
| KR | 102220243 B1 | * | 2/2021 | ............... A61B 5/01 |
| WO | 2014/031800 A1 | | 2/2014 | |
| WO | WO-2022170957 A1 | * | 8/2022 | ............ F04B 49/065 |

OTHER PUBLICATIONS

International Search Report and Written Opinion received in PCT/US2022/050389 mailed Mar. 10, 2023.
(Continued)

*Primary Examiner* — Laert Dounis
(74) *Attorney, Agent, or Firm* — Meunier Carlin & Curfman LLC

(57)    ABSTRACT

Systems and methods for testing a pump assembly for a cooled radiofrequency treatment procedure. In some embodiments, the pump assembly and at least one pump head are driven by at least one respective motor, where the at least one pump head is coupled to tubing for delivering a cooling fluid to a medical probe assembly. The at least one pump head is configured to pump the cooling fluid through the tubing for the cooled radiofrequency treatment proce-
(Continued)

dure. The system can also include a programmable controller operatively connective to the pump assembly and configured to control the pump assembly, and one or more pump function sensors for sensing operation parameters associated with the pump assembly and communicating the pump operation parameters to the controller. The controller can determine that the pump assembly is operating properly based on the operation parameters and can adjust the operation of the motor or output an alert.

26 Claims, 11 Drawing Sheets

(51) Int. Cl.
    *A61B 18/00*         (2006.01)
    *A61B 18/12*         (2006.01)
    *A61B 18/14*         (2006.01)
    *F04B 43/12*         (2006.01)

(52) U.S. Cl.
    CPC ............... *A61B 2017/00119* (2013.01); *A61B 2018/00005* (2013.01); *A61B 2018/00011* (2013.01); *A61B 2018/00023* (2013.01); *A61B 2018/00339* (2013.01); *A61B 2018/00434* (2013.01); *A61B 2018/00577* (2013.01); *A61B 2018/00642* (2013.01); *A61B 2018/00744* (2013.01); *A61B 2018/00791* (2013.01); *A61B 2018/00863* (2013.01)

(58) Field of Classification Search
    CPC .......................... A61B 2018/1213–167; A61B 2017/00119–00123
    See application file for complete search history.

(56)              References Cited

U.S. PATENT DOCUMENTS

| | | | |
|---|---|---|---|
| 11,369,434 B2 * | 6/2022 | Brannan | ............ A61B 18/1815 |
| 2004/0267340 A1 * | 12/2004 | Cioanta | ................... A61F 7/123 |
| | | | 607/113 |
| 2013/0267892 A1 | 10/2013 | Woolford | |
| 2017/0281215 A1 | 10/2017 | Stoddard et al. | |
| 2019/0201045 A1 | 7/2019 | Yates et al. | |
| 2020/0205886 A1 | 7/2020 | Wang | |
| 2020/0330153 A1 * | 10/2020 | Cosman, Jr. | ....... A61B 18/1206 |
| 2021/0045792 A1 * | 2/2021 | Wang | .................... A61B 18/02 |

OTHER PUBLICATIONS

Extended European Search Report from corresponding EP228986519.0, dated Jul. 29, 2025, 9 pages.

* cited by examiner

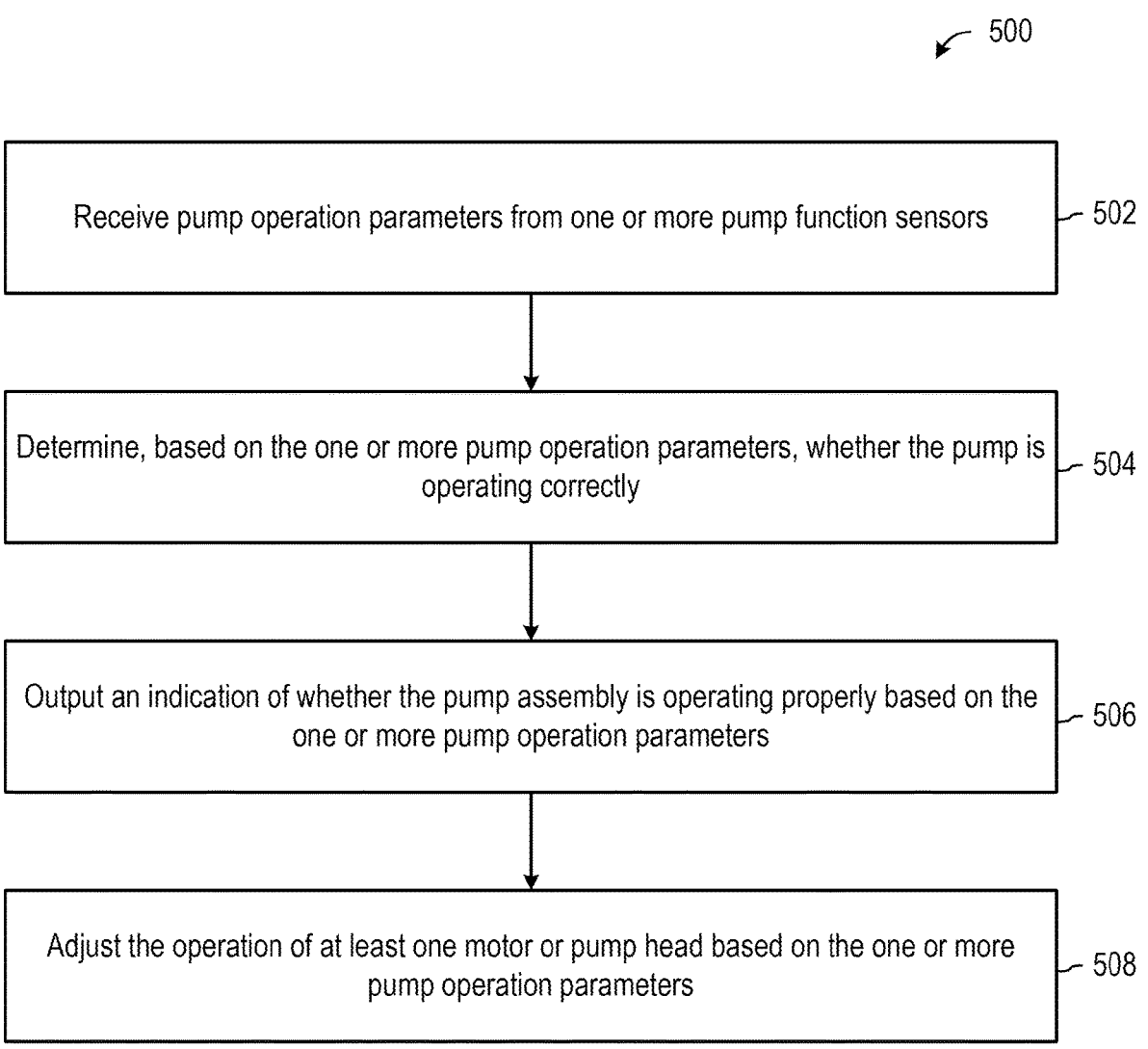

500

Receive pump operation parameters from one or more pump function sensors — 502

Determine, based on the one or more pump operation parameters, whether the pump is operating correctly — 504

Output an indication of whether the pump assembly is operating properly based on the one or more pump operation parameters — 506

Adjust the operation of at least one motor or pump head based on the one or more pump operation parameters — 508

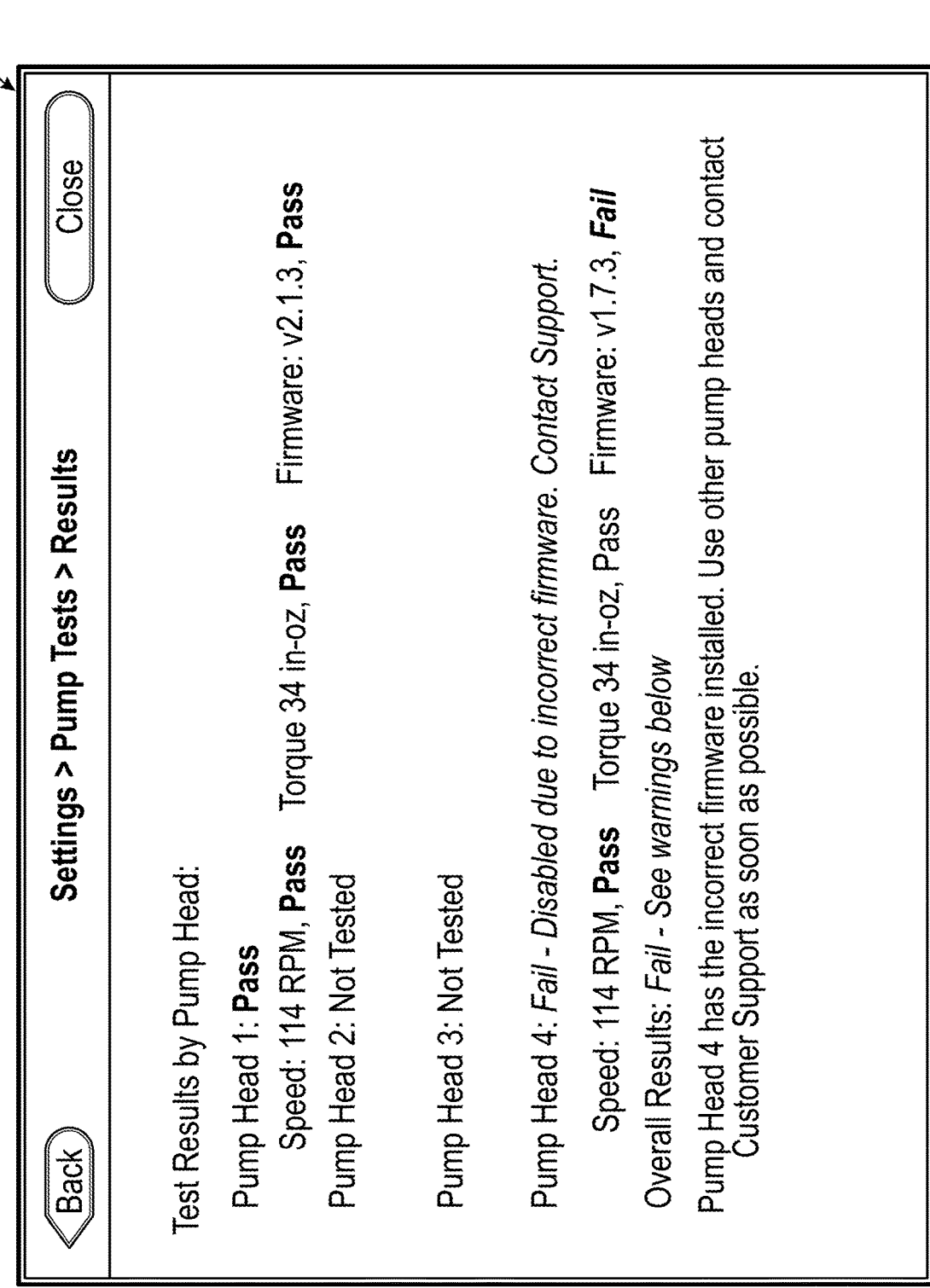

Back          Settings > Pump Tests > Results          Close

Test Results by Pump Head:

Pump Head 1: Pass

Speed: 114 RPM, Pass      Torque 34 in-oz, Pass      Firmware: v2.1.3, Pass

Pump Head 2: Not Tested

Pump Head 3: Not Tested

Pump Head 4: *Fail - Disabled due to incorrect firmware. Contact Support.*

Speed: 114 RPM, Pass      Torque 34 in-oz, Pass      Firmware: v1.7.3, *Fail*

Overall Results: *Fail - See warnings below*

Pump Head 4 has the incorrect firmware installed. Use other pump heads and contact Customer Support as soon as possible.

FIG. 8

SYSTEMS, DEVICES, AND METHODS RELATING TO A COOLED RADIOFREQUENCY TREATMENT PROCEDURE

CROSS-REFERENCE TO RELATED APPLICATIONS

This application is a U.S. National Stage application filed under 35 U.S.C. § 371 of PCT/US2022/050389, filed Nov. 18, 2022, which claims the benefit of and priority to U.S. Provisional Patent App. No. 63/281,241, filed Nov. 19, 2021, the contents of which are incorporated herein by reference in their entirety.

BACKGROUND

Lower back injuries and chronic joint pain are major health problems resulting not only in debilitating conditions for the patient, but also in the consumption of a large proportion of funds allocated for health care, social assistance and disability programs. In the lower back, disc abnormalities and pain may result from trauma, repetitive use in the workplace, metabolic disorders, inherited proclivity, and/or aging. The existence of adjacent nerve structures and innervation of the disc are very important issues in respect to patient treatment for back pain. In joints, osteoarthritis is the most common form of arthritis pain and occurs when the protective cartilage on the ends of bones wears down over time.

A minimally invasive technique of delivering high-frequency electrical current has been shown to relieve localized pain in many patients. Generally, the high-frequency current used for such procedures is in the radiofrequency (RF) range, i.e., between 100 kHz and 1 GHz and more specifically between 300-600 kHz. The treatment of pain using high-frequency electrical current has been applied successfully to various regions of patients' bodies suspected of contributing to chronic pain sensations. In addition to creating lesions in neural structures, application of radiofrequency energy has also been used to treat tumors throughout the body.

The RF electrical current is typically delivered from a generator via connected electrodes that are placed in a patient's body, in a region of tissue that contains a neural structure suspected of transmitting pain signals to the brain. The electrodes generally include one of more probes defining an insulated shaft with an exposed conductive active electrode tip to deliver the radiofrequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to affecting a neural structure's ability to transmit signals and usually results in the complete inability of a neural structure to transmit signals, thus removing the pain sensations.

To extend the size of a lesion, radiofrequency treatment may be applied in conjunction with a cooling mechanism, whereby a cooling means is used to reduce the temperature of the tissue near an energy delivery device, allowing a higher voltage to be applied without causing an unwanted increase in local tissue temperature. The application of a higher voltage allows regions of tissue further away from the energy delivery device to reach a temperature at which a lesion can form, thus increasing the size/volume of the lesion compared to conventional (non-cooling) radiofrequency treatments, where the larger size/volume of the lesion can increase the probability of success of ablating a target nerve. Cooled radiofrequency ablation is achieved by delivering, in a closed-loop circulation, cooling fluid (e.g., sterile water) via a peristaltic pump through the probe/active electrode. The cooling fluid continuously transfers heat away from the active electrode, allowing the electrode-tissue interface temperature to be maintained at a level that does not char or significantly desiccate the surrounding tissue, which is the primary limitation of conventional radiofrequency ablation. As a result, more radiofrequency energy can be delivered to the tissue, creating a lesion having a larger volume/size compared to a lesion created by conventional radiofrequency ablation.

If the supply of cooling fluid to the probe/active electrode is disrupted, it can result in an unwanted increase in local tissue temperature. For example, the failure of one or more pump units may require that the probe/active electrode be disabled, and/or the treatment be discontinued.

It is with respect to these and other considerations that the various embodiments described below are presented.

SUMMARY

In some aspects, the present disclosure relates to systems, devices and methods relating to cooled radiofrequency procedures, such as for use in RF ablation probe cooling.

In one aspect, the present disclosure relates to a system for testing a pump assembly for a cooled radiofrequency (RF) treatment procedure, which in one embodiment, includes a pump assembly and at least one pump head driven by at least one respective motor, where the at least one pump head is coupled to tubing for delivering a cooling fluid to a medical probe assembly, and where the at least one pump head is configured to pump the cooling fluid through the tubing for the cooled RF treatment procedure. The system also includes a programmable controller operatively connective to the pump assembly and configured to control the pump assembly, and one or more pump function sensors for sensing operation parameters associated with the pump assembly and communicating the pump operation parameters to the controller, where the pump operation parameters indicate whether the pump assembly is operating properly, and where the pump operation parameters include an indication, from the one or more pump function sensors, of at least one parameter associated with the rotation of the pump head or at least one parameter associated with power provided to the pump assembly, where the controller is configured to determine, based on the sensed pump operation parameters, whether the pump assembly is operating properly and/or is configured properly, and where the controller is configured to perform at least one of: outputting an indication, for display, at least one of the pump operation parameters; or responsive to determining that the pump assembly is not operating properly and/or is not configured properly, performing at least one of: adjusting operation of at least one of the at least one respective motor, at least one pump head, or the power provided to the pump assembly, such that the pump assembly operates properly and such that the cooling system is a closed loop feedback system; or outputting an alert.

In one embodiment, the one or more pump function sensors include one or more of a torque sensor, rotary encoder, acceleration sensor, or sensor to detect current.

In one embodiment, the one or more pump function sensors include a non-invasive fluid flow sensor.

In one embodiment, the one or more pump operation parameters include flow rate.

In one embodiment, the at least one parameter associated with the rotation of the pump head includes at least one of rotational position, RPM, torque, rotation speed, or acceleration.

In one embodiment, the at least one parameter associated with power provided to the pump assembly includes a parameter associated with current provided to the pump assembly.

In one embodiment, the at least one parameter associated with power provided to the pump assembly includes a temperature of the at least one respective motor.

In one embodiment, determining, by the controller, whether the pump assembly is operating properly and/or is configured properly includes comparing the sensed pump operation parameters to corresponding predetermined parameters associated with proper operation.

In one embodiment, the one or more pump function sensors further include at least one of a flow rate sensor or a back pressure sensor, configured to sense one or more parameters associated with flow rate of the cooling fluid.

In one embodiment, the pump assembly is a peristaltic pump assembly.

In one embodiment, the system further includes a sensed output component that is configured to output, to a log, the sensed pump operation parameters for diagnostics and/or troubleshooting.

In one embodiment, the system further includes a user interface configured to receive user input that is associated with the pump assembly test, the user interface being configured to provide the user input to the controller.

In one embodiment, the system further includes a user interface configured to output, for display, at least one of the one or more of the sensed parameters associated with the pump operation parameters.

In one embodiment, the system further includes a graphical user interface configured to display, to a user, at least one visual representation of the sensed parameters associated with the pump operation parameters or the alert.

In one aspect, the present disclosure relates to a method for testing a pump assembly for a cooled radiofrequency (RF) treatment procedure, which in one embodiment includes delivering, by tubing coupled to at least a pump assembly including at least one pump head for driving the at least one pump head, a cooling fluid to a medical probe assembly, for the cooled RF treatment procedure, and controlling, by a programmable controller operatively connected to the pump assembly, functions of the pump assembly. The method also includes sensing, by one or pump function sensors, operation parameters associated with the pump assembly and communicating the pump operation parameters to the controller, where the pump operation parameters indicate whether the pump assembly is operating properly, and where the pump operation parameters include an indication, from the one or more pump function sensors, of at least one parameter associated with the rotation of the pump head or at least one parameter associated with power provided to the pump assembly, and determining, by the controller and based on the sensed pump operation parameters, whether the pump assembly is operating properly and/or is configured properly. The method also includes outputting, an indication, for display, at least one of the pump operation parameters; or responsive to determining, by the controller, that the pump assembly is not operating properly and/or is not configured properly, performing at least one of: adjusting, by the controller, operation of at least one of the at least one respective motor, at least one pump head, or the power provided to the pump assembly, such that the pump assembly operates properly and such that the cooling system is a closed loop feedback system; or outputting, by the controller, an alert.

In one embodiment, the one or more pump function sensors include one or more of a torque sensor, rotary encoder, acceleration sensor, or sensor to detect current.

In one embodiment, the one or more pump function sensors include a non-invasive fluid flow sensor.

In one embodiment, the one or more pump operation parameters include flow rate.

In one embodiment, the at least one parameter associated with the rotation of the pump head includes at least one of rotational position, RPM, torque, rotation speed or acceleration.

In one embodiment, the at least one parameter associated with power provided to the pump assembly includes a parameter associated with current provided to the pump assembly.

In one embodiment, the at least one parameter associated with power provided to the pump assembly includes a temperature of the at least one respective motor.

In one embodiment, the method includes determining, by the controller, whether the pump assembly is operating properly and/or is configured properly includes comparing the sensed pump operation parameters to corresponding predetermined parameters associated with proper operation.

In one embodiment, the method includes sensing, by one or more pump function sensors, one or more parameters associated with flow rate of the cooling fluid, where the one or more pump function sensors include at least one of a flow rate sensor or a back pressure sensor.

In one embodiment, the method includes sensing, by the one or more pump function sensors, one or more parameters associated with flow rate of the cooling fluid.

In one embodiment, the method includes outputting, to a log, the sensed pump operation parameters for diagnostics and/or troubleshooting.

In one embodiment, the method includes receiving, by the controller and via a user interface, a user input that is associated with the pump assembly test, the user interface being configured to provide the user input to the controller.

In one embodiment, the method includes outputting, by the controller and for display via a user interface, at least one of the one or more of the sensed parameters associated with the pump operation parameters.

In one embodiment, the method includes displaying, by the controller and for display via a user interface, at least one visual representation of the sensed parameters associated with the pump operation parameters or the alert.

Other aspects and features according to the example embodiments of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 5A is a flow chart of a method for performing a pump test, according to some embodiments.

FIGS. 8 and 9 are an example user interfaces for reviewing the results of a pump test, according to some embodiments.

DETAILED DESCRIPTION

Figure 1:
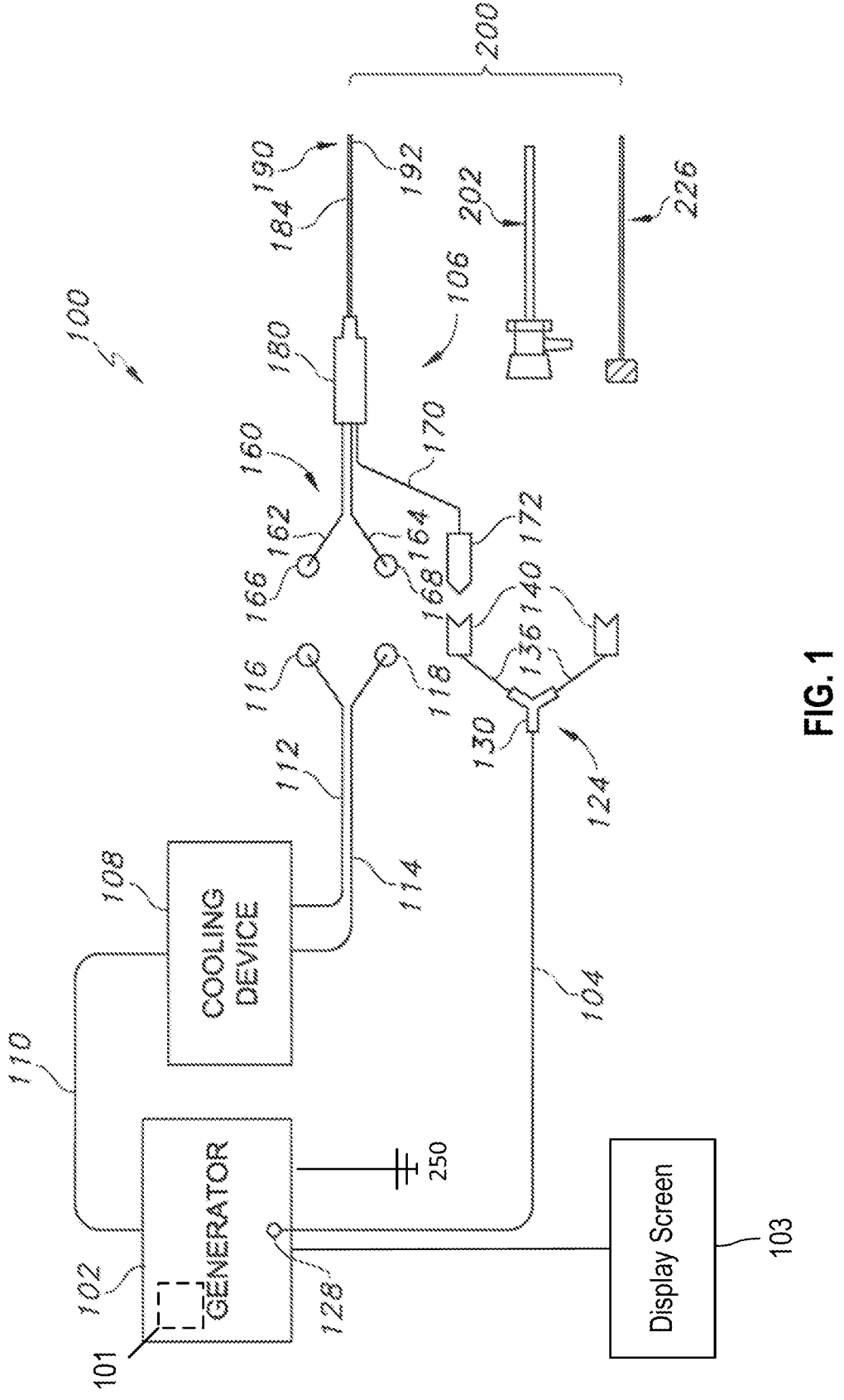
FIG. 1 is a diagram of an example system for applying cooled radiofrequency (RF) electrical energy to target tissue in a subject's body, including a probe assembly and one or more cooling devices, and a grounding pad, according to some embodiments.

In some aspects, the disclosed technology relates to systems, systems, devices and methods relate to cooled radiofrequency treatment procedures. Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific organs, tissues, or fluids of a subject, may be in a particular location of the subject, which may be referred to herein as an "area of interest", "region of interest", or "target location". For the purposes of the present disclosure, a lesion refers to any effect achieved through the application of energy to a tissue in a patient's body, and the disclosure is not intended to be limited in this regard. Furthermore, for the purposes of this description, proximal generally indicates that portion of a device or system next to or nearer to a user (when the device is in use), while the term distal generally indicates a portion further away from the user (when the device is in use).

Reference will now be made in detail to one or more embodiments of the present disclosure, examples of which are illustrated in the drawings. Each example and embodiment is provided by way of explanation of the disclosure, and is not meant as a limitation of the disclosure. For example, features illustrated or described as part of one embodiment may be used with another embodiment to yield still a further embodiment. It is intended that the disclosure include these and other modifications and variations as coming within the scope and spirit of the disclosure.

Generally speaking, the present disclosure in some embodiments is directed to a cooled radiofrequency ablation system. The system includes a probe assembly having a proximal region, a distal tip region, and a hollow elongated shaft. The hollow elongated shaft defines an internal cavity, and a first internal cooling fluid tube and a second internal cooling fluid tube are positioned inside the internal cavity and extend from the proximal region. Further, the distal tip region includes a conductive portion for delivering energy to a target location within tissue. The system also includes a radiofrequency generator for delivering energy to the target location within tissue via the conductive portion of the distal tip region of the probe assembly, as well as a cooling device including a cooling fluid reservoir and a bidirectional pump assembly operable to circulate a cooling fluid from the cooling fluid reservoir through the first internal cooling fluid tube, the internal cavity, the second internal cooling fluid tube, and back to the cooling fluid reservoir when the bidirectional pump is operating in a first direction; or from the cooling fluid reservoir through the second internal cooling fluid tube, the internal cavity, the first internal cooling fluid tube, and back to the cooling fluid reservoir when the bidirectional pump is operating in a second direction. The various features of the cooled radiofrequency ablation system will now be discussed in more detail in reference to FIGS. 1-6.

Turning first to FIG. 1, a schematic diagram of an energy delivery system 100 for the delivery of energy, such as RF energy, to a target location of tissue of a patient is provided and is presented herein for purposes of describing an exemplary operating environment in which the present introducer and assembly may be used. The system 100 includes a generator 102, a display screen 103, a cable 104, one or more probe assemblies 106 (only one probe assembly is shown), one or more cooling devices 108 that include a one or more cooling fluid reservoirs (not shown), and a bidirectional pump assembly 120 (see FIG. 2), a pump cable 110, one or more proximal cooling fluid supply tubes 112, and one or more proximal cooling fluid return tubes 114. Throughout the present disclosure, the term "pump assembly" may be used interchangeably with "pump unit."

The generator 102 may be a radiofrequency (RF) generator, or any other energy source, such as microwave energy, thermal energy, ultrasound, or optical energy. The generator 102 may be connected to display screen 103 that displays various visual representations related to a treatment procedure, such as any parameters that are relevant to a treatment procedure, for example temperature, impedance, etc., and errors or warnings related to a treatment procedure. In some embodiments, display screen 103 is part of generator 102. For example, display screen 103 may be physically mounted on generator 102. Display screen 103 may be any suitable screen type, such as an LCD or LED display, a touchscreen, etc. Alternatively, the generator 102 may include means of transmitting a signal to an external display. For example, in some such embodiments, display screen 103 may be external to generator 102 and/or may be a component of a separate computing device. The generator 102 is operable to communicate with the first and second probe assemblies 106 and the one or more cooling devices 108. Such communication may be unidirectional or bidirectional depending on the devices used and the procedure performed.

In addition, as shown, a distal region 124 of the cable 104 may include a splitter 130 that divides the cable 104 into two distal ends 136 such that the probe assemblies 106 can be connected thereto. A proximal end 128 of the cable 104 is connected to the generator 102. This connection can be permanent, whereby, for example, the proximal end 128 of the cable 104 is embedded within the generator 102, or temporary, whereby, for example, the proximal end 128 of cable 104 is connected to generator 102 via an electrical connector. The two distal ends 136 of the cable 104 terminate in connectors 140 operable to couple to the probe assemblies 106 and establish an electrical connection between the probe assemblies 106 and the generator 102. In alternate embodiments, the system 100 may include a separate cable for each probe assembly 106 being used to couple the probe assemblies 106 to the generator 102.

The cooling device(s) 108 may include any means of reducing a temperature of material located at and proximate to one or more of the probe assemblies 106. For example, the cooling devices 108 may include a pump assembly 120 (see FIG. 2), such as a bidirectional pump assembly, operable to circulate a fluid from the cooling devices 108 through one or more proximal cooling fluid supply tubes 112, the probe assemblies 106 (e.g., through an internal cavity 122 of the probe assemblies 106, one or more proximal cooling fluid return tubes 114, and back to the one or more cooling devices 108.

The system 100 may include a programmable controller (which may also be referred to herein as simply a "controller") for facilitating communication between the cooling devices 108 and the generator 102, via a feedback control loop. The feedback control may be implemented, for example, in a control module which may be a component of the generator 102. In such embodiments, the generator 102 is operable to communicate bidirectionally with the probe assemblies 106 as well as with the cooling devices 108, wherein bidirectional communication refers to the capability of a device to both receive a signal from and send a signal to another device.

As an example, the generator 102 may receive temperature measurements from one or both of the first and second probe assemblies 106. Based on the temperature measurements, the generator 102 may perform some action, such as modulating the power that is sent to the probe assemblies 106. Thus, both probe assemblies 106 may be individually controlled based on their respective temperature measurements.

The pumps associated with the cooling devices 108 may communicate a fluid flow rate to the generator 102 and may receive communications from the generator 102 instructing the pumps to modulate this flow rate. With the cooling devices 108 turned off, any temperature sensing elements associated with the probe assemblies 106 would not be affected by the cooling fluid allowing a more precise determination of the surrounding tissue temperature to be made. In addition, when using more than one probe assembly 106, the average temperature or a maximum temperature in the temperature sensing elements associated with probe assemblies 106 may be used to modulate cooling. The cooling devices 108 may reduce the rate of cooling or disengage depending on the distance between the probe assemblies 106. For example, when the distance is small enough such that a sufficient current density exists in the region to achieve a desired temperature, little or no cooling may be required. In such an embodiment, energy is preferentially concentrated between first and second energy delivery devices 192 through a region of tissue to be treated, thereby creating a strip lesion characterized by an oblong volume of heated tissue that is formed when an active electrode is in close proximity to a return electrode of similar dimensions.

The cooling devices 108 may also communicate with the generator 102 to alert the generator 102 to one or more possible errors and/or anomalies associated with the cooling devices 108. For example, if cooling flow is impeded or if a lid of one or more of the cooling devices 108 is opened. The generator 102 may then act on the error signal by at least one of alerting a user, aborting the procedure, and modifying an action. Still referring to FIG. 1, the proximal cooling fluid supply tubes 112 may include proximal supply tube connectors 116 at the distal ends of the one or more proximal cooling fluid supply tubes 112. Additionally, the proximal cooling fluid return tubes 114 may include proximal return tube connectors 118 at the distal ends of the one or more proximal cooling fluid return tubes 114. In one embodiment, the proximal supply tube connectors 116 are female Luer-lock type connectors and the proximal return tube connectors 118 are male Luer-lock type connectors although other connector types are intended to be within the scope of the present disclosure. In addition, as shown in FIG. 1, the probe assembly 106 may include a proximal region 160, a handle 180, a hollow elongate shaft 184, which can also be referred to as an electrocap, and a distal tip region 190 that includes the one or more energy delivery devices 192 and that can also be referred to as the active tip. The elongate shaft 184 may be manufactured out of polyimide, which provides exceptional electrical insulation while maintaining sufficient flexibility and compactness. In alternate embodiments, the elongate shaft 184 may be any other material imparting similar qualities. In still other embodiments, the elongate shaft 184 may be manufactured from an electrically conductive material and may be covered by an insulating material so that delivered energy remains concentrated at the energy delivery device 192 of the distal tip region 190. The proximal region 160 includes a distal cooling fluid supply tube 162, a distal supply tube connector 166, a distal cooling fluid return tube 164, a distal return tube connector 168, a probe assembly cable 170, and a probe cable connector 172. In such embodiments, the distal cooling fluid supply tube 162 and distal cooling fluid return tube 164 are flexible to allow for greater maneuverability of the probe assemblies 106, but alternate embodiments with rigid tubes are possible.

The distal supply tube connector 166 may be a male Luer-lock type connector and the distal return tube connector 168 may be a female Luer-lock type connector. Thus, the proximal supply tube connector 116 may be operable to interlock with the distal supply tube connector 166 and the proximal return tube connector 118 may be operable to interlock with the distal return tube connector 168.

The probe cable connector 172 may be located at a proximal end of the probe assembly cable 170 and may be operable to reversibly couple to one of the connectors 140, thus establishing an electrical connection between the generator 102 and the probe assembly 106. The probe assembly cable 170 includes one or more conductors to transmit RF current from the generator 102 to the one or more energy delivery devices 192, as well as to connect multiple temperature sensing devices to the generator 102 as discussed below.

The energy delivery devices 192 may include any means of delivering energy to a region of tissue adjacent to the distal tip region 190. For example, the energy delivery devices 192 may include an ultrasonic device, an electrode or any other energy delivery means and the invention is not limited in this regard. Similarly, energy delivered via the energy delivery devices 192 may take several forms including but not limited to thermal energy, ultrasonic energy, radiofrequency energy, microwave energy or any other form of energy. For example, in one embodiment, the energy delivery devices 192 may include an electrode. The active region of the electrode may be 2 to 20 millimeters (mm) in length and energy delivered by the electrode is electrical energy in the form of current in the RF range. The size of the active region of the electrode can be optimized for placement within an intervertebral disc, however, different sizes of active regions, all of which are within the scope of the present invention, may be used depending on the specific procedure being performed. In some embodiments, feedback from the generator 102 may automatically adjust the exposed area of the energy delivery device 192 in response to a given measurement such as impedance or temperature. For example, in one embodiment, the energy delivery devices 192 may maximize energy delivered to the tissue by implementing at least one additional feedback control, such as a rising impedance value.

FIG. 1 also depicts an introducer 202 and a stylet 226, wherein the combination of the RF probe assembly 106, the introducer 202, and the stylet 226 define an RF ablation probe system 200 in accordance with aspects of the present invention.

Figure 2:
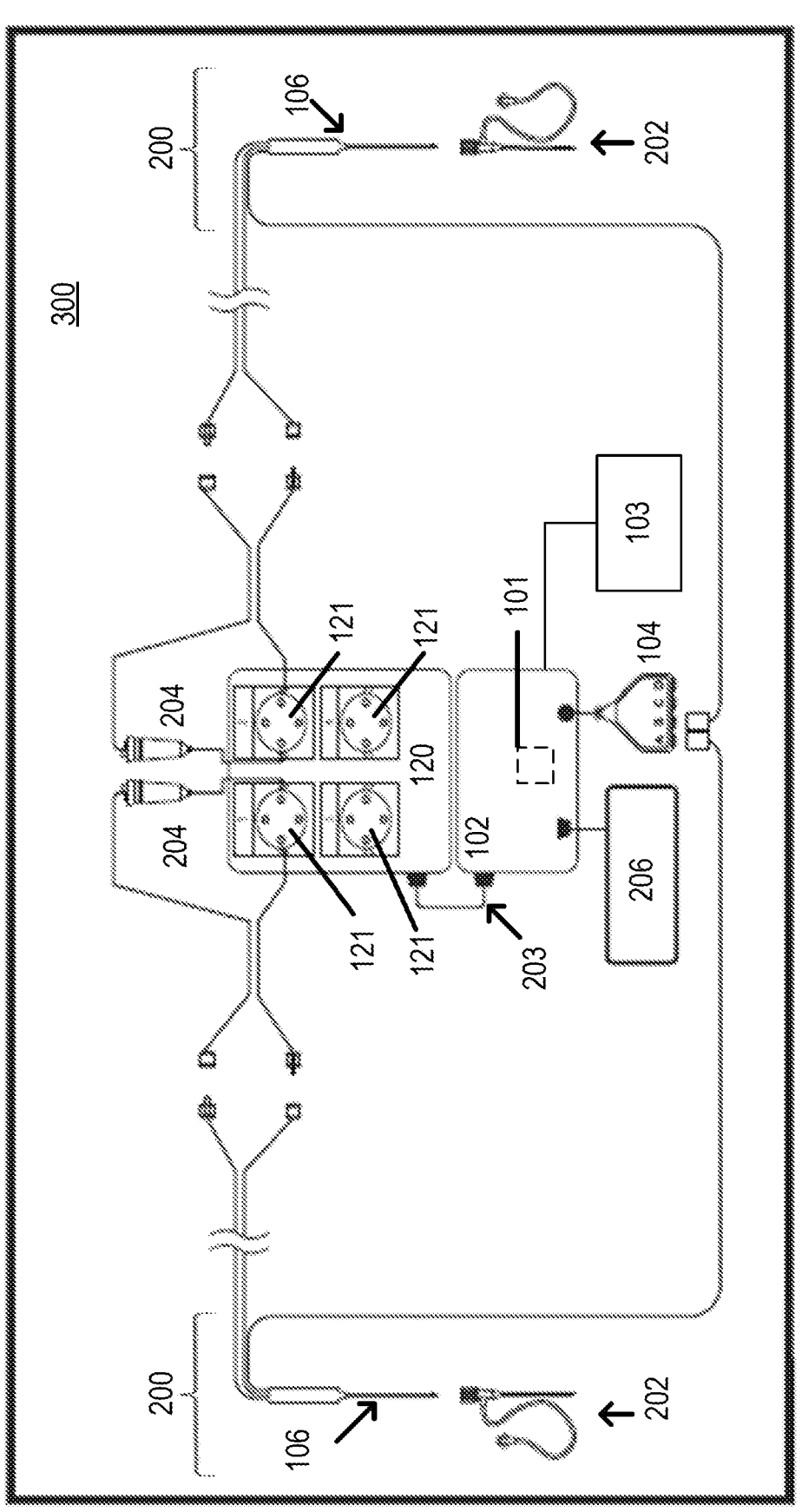
FIG. 2 is a diagram of an alternate system for applying cooled RF electrical energy to a subject, which includes a quad pump unit and is configured for a two-probe connection, according to some embodiments.

FIG. 2 illustrates a system capable of performing a cooled radiofrequency (RF) treatment procedure. According to some embodiments of the present disclosure, the system includes a pump assembly 120 and a generator 102. The pump 120 assembly can include different numbers of pump heads 121. Different numbers of pump heads 121 can be used in different embodiments of the present disclosure, in combinations with different numbers of probe systems 200. The pump heads 121 can be configured to move a cooling fluid through one or more tubes connected to a medical probe system 200.

Figure 3:
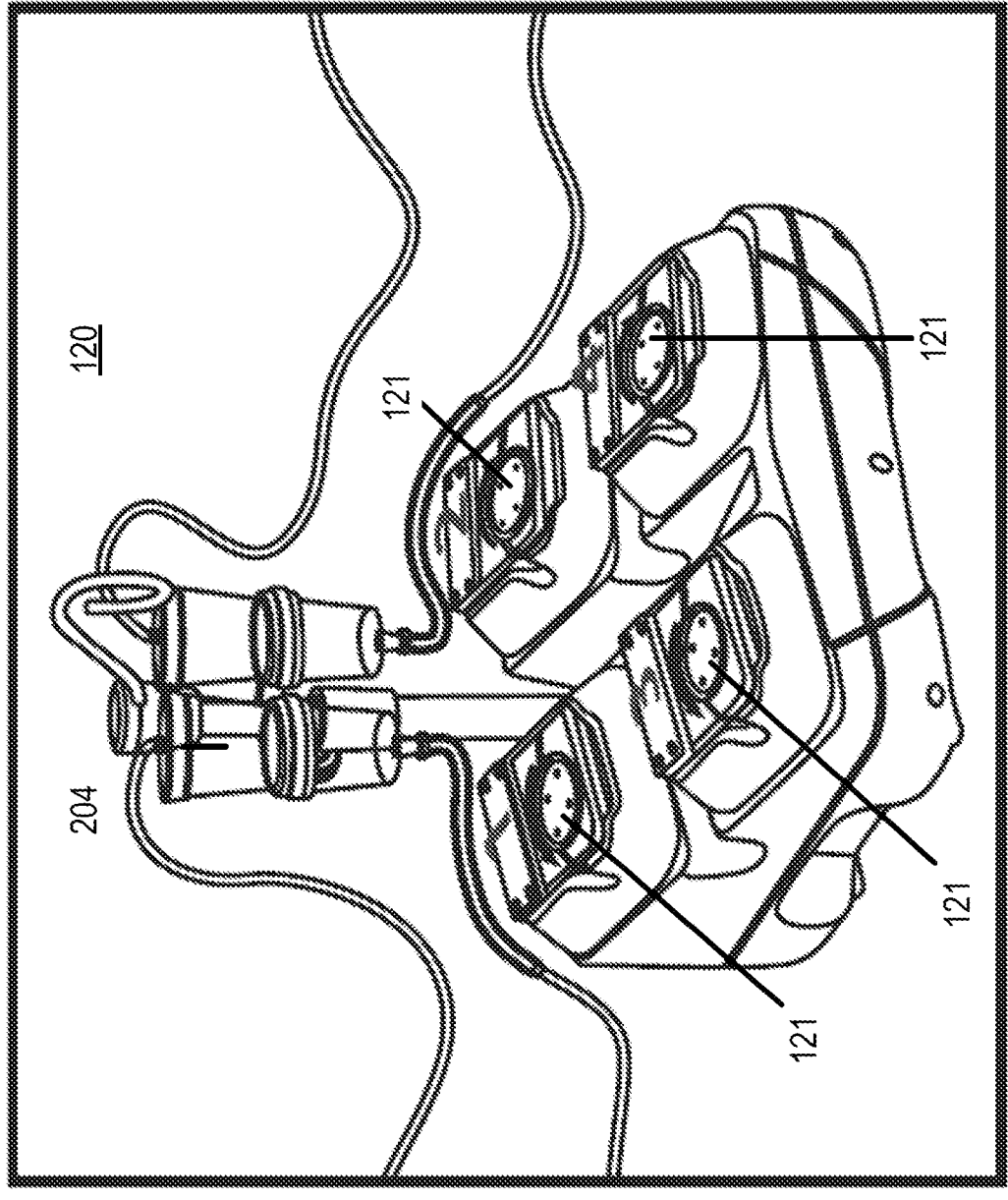
FIG. 3 is a diagram of a quad pump unit as used in the system of FIG. 2, according to some embodiments.
Figure 4:
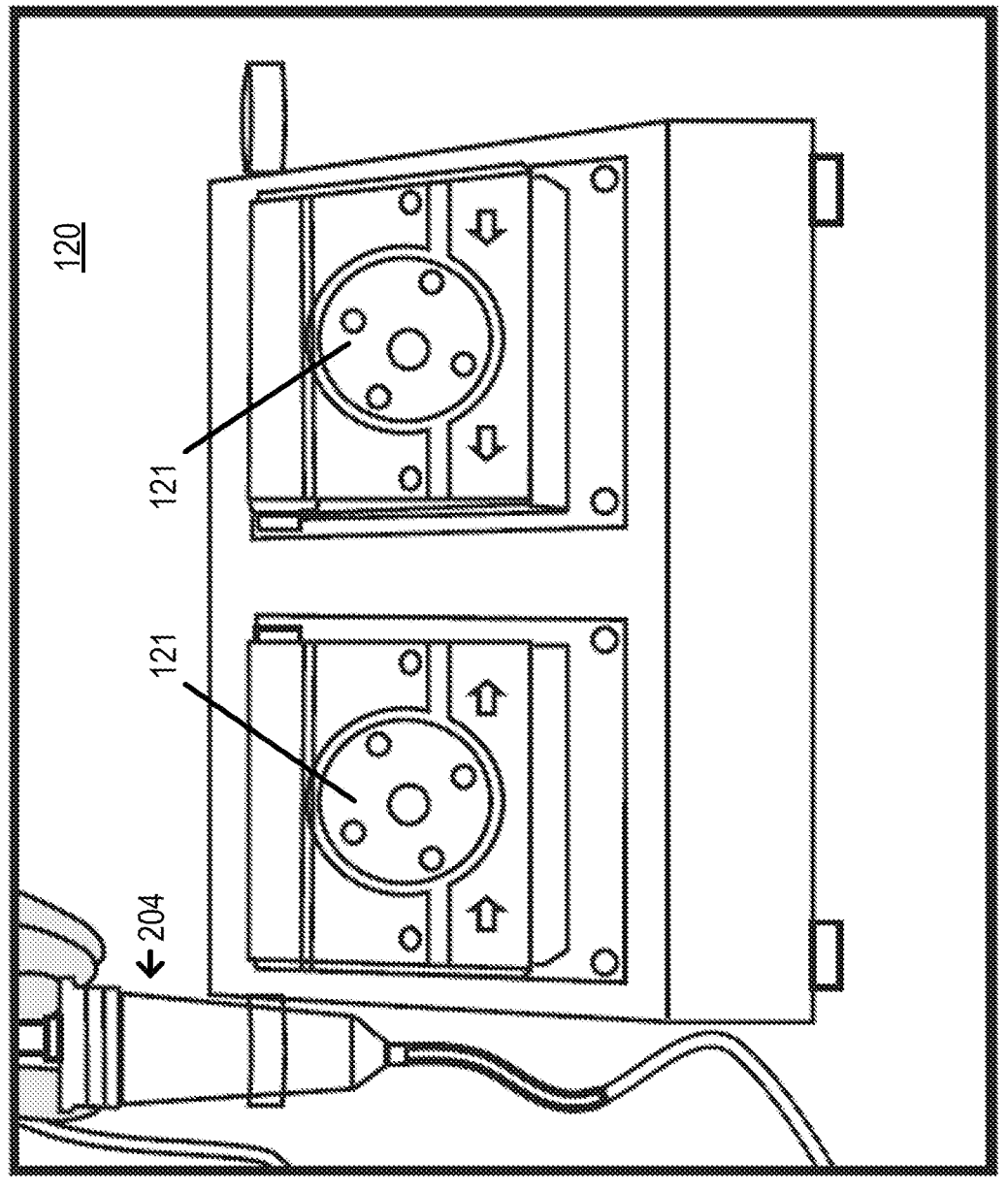
FIG. 4 is a diagram of a dual pump unit as used in the system of FIG. 2, according to some embodiments.

The present disclosure contemplates that any number of pump heads 121 can be used in the pump assembly 120. In some embodiments of the present disclosure, the pump assembly 120 includes two pump heads 121 (a "dual pump unit"). In other embodiments of the present disclosure, the pump assembly 120 includes four pump heads 121 (a "quad pump unit"). A perspective view of a quad pump unit is shown in FIG. 3, and a front-view of a dual-pump unit is shown in FIG. 4. In some embodiments of the present disclosure, the pump heads 121 can be peristaltic pump heads 121, as shown in FIGS. 3 and 4. Tubing can be connected to the peristaltic pump heads 121 by inserting the tubing into the peristaltic pump heads 121. In some embodiments of the present disclosure, each pump head 121 includes a motor, which drives the pump head 121, pumping the cooling fluid through the tubing for a cooled RF treatment procedure.

As shown in the embodiment of the present disclosure shown in FIG. 2, the system 300 can include two probe systems 200 and a grounding pad 206. The pump heads 121 of the pump assembly 120 move cooling fluid through tubing and to the probe assemblies 106. In the embodiment shown in FIG. 2, the pump assembly 120 is a four-pump pump unit ("quad pump unit" or "QPU"). The cooling fluid can exit through a second length of tubing and a burette 204 to return to one of the pump heads 121 of the pump assembly 120. In some embodiments of the present disclosure, each pump head 121 is configured to supply cooling fluid to one probe assembly 106 although it is contemplated that in other embodiments the numbers of probe assemblies 106 and pump heads 121 can be different. For example, in the embodiment of the present disclosure shown in FIG. 2, the pump assembly 120 includes four pump heads 121 but only two are active (shown as not connected to the probe assemblies 201 or burettes 204).

Additional configurations of probe assemblies 106 are contemplated by the present disclosure, and the two-probe configuration shown in FIG. 2 is intended only as a non-limiting example. Non-limiting examples of other probe configurations include one-probe, three probe, and four probe configurations.

The generator 102 and/or pump assembly 120 can be configured to implement the method disclosed by FIG. 5A, described in further detail below. In some embodiments of the present disclosure, the generator 102 and/or pump assembly 120 can include one or more components of the computer 600 shown in FIG. 6. An electrical connection 203 between the generator 102 and pump unit 120 can be used to transmit sensor information between the generator 102 and pump unit 120. The electrical connection 203 can also be used by the generator 102 and/or pump assembly 120 to send control signals to each other. Additionally, instructions and user inputs can pass from the generator 102 to the pump unit 120 or vice versa. In the embodiment depicted in FIG. 2, the controller 101 is part of the generator 102. The generator 102 and/or controller 101 can determine information identifying the pump assembly 120 using resistor ID, device ID stored in a memory unit on a computing device within the pump (e.g., a computing device 600) by a network connection (e.g., SSL, Bluetooth, Wi-Fi) or by a serial communication signal (e.g., I2C, Serial/RS232). Alternatively or additionally, the generator 102 and/or controller 101 can determine identifying information related to for some or all of the motors and/or motor controllers included in the pump assembly 120. In some embodiments of the present disclosure, each motor that is part of the pump assembly 120 includes a separate motor controller corresponding to that motor, and the motor controllers are separate controllers from the controller 101. However, it should be understood that the present disclosure contemplates that the motor controllers can be integrated into the generator 102, controller 101, or that one motor controller can be used for multiple or all of the motors that are part of the pump assembly 120.

Based on the pump information, the generator 102 can determine the modes that the pump assembly 120 or individual pump heads 121 can be used in. These modes can correspond to different treatment operations. Throughout the present disclosure the term "mode" or "modes of operation" refers to the programmed operations of the generator and pump assembly 120 corresponding to different treatments that the systems 100, 300 can be used for with respect to performing a treatment procedure on a subject.

The pump assembly 120 can include one or more pump function sensors for sensing operation parameters associated with the pump assembly 120 and communicating the pump operation parameters to the controller 101. The operation parameters can include "pump data" corresponding to different operation parameters associated with the pumps and/or pump motors. The pump operation parameters and/or pump data can indicate whether the pump assembly 120 is operating properly. In some embodiments of the present disclosure, the pump function sensors include one or more of a torque sensor, rotary encoder, acceleration sensor, a sensor to detect a change in current, a flow rate sensor, and/or or a back pressure sensor.

The pump data collected by the pump sensors can include mechanical and electrical information about the performance of the one or more pump heads 121. Non-limiting examples of the pump data include torque speed, rotational speed, flow rate, back pressure, acceleration, and change in current.

Torque can be used to determine if a pump head 121 is operating correctly. The RPM of the pump head 121 can be measured, and the measure of torque at a certain pump head speed (measured in RPM) can be compared to a pre-determined range based on the configuration of the pump (e.g., pump type and/or pump mode). If the torque is higher than the pre-determined range, it can indicate that the pump head 121 has stalled and/or that the pump motor is damaged. Further, a torque higher than the pre-determined range can indicate that the pump heads 121 are improperly loaded, or that the probe assemblies 106 are improperly configured. Alternatively, if the torque is below the pre-determined range, it can indicate that the pump head 121 is empty, either because there is no cooling fluid, or because no tube has been inserted into the pump head 121. Both high and low torque values can cause the system to display a warning (e.g., via display screen 103), and the warning can depend on the speed and torque values.

High and/or low torque values can also be used in some embodiments of the present disclosure as a control input to the pump unit 120 and/or generator 102. For example, a high torque value can indicate that the pump head 121 is damaged and indicate that the pump is providing less coolant flow than designed. The controller 101 can detect that the pump head 121 is damaged by detecting the high torque value. The controller 101 can then take steps to compensate for the reduced cooling fluid flow. For example, the generator 102 can reduce the electrical current applied to reduce heating. Alternatively, if the torque is below the pre-determined range, the generator 102 can be disabled so that RF energy is not applied to a patient without the probe system 200 being cooled.

Rotational speed values of the one or more pump heads 121 can also be used in some embodiments of the present disclosure. A pre-determined speed range can be measured for different models of pump. If the speed is lower than the pre-determined speed range, it can indicate that the pump head 121 is stalled or defective.

In some embodiments of the present disclosure, current data can also be collected from the one or more pump motors that are part of the pump head 121. The idle current of the pump motor can be compared to a predetermined expected range, and when the idle current is outside that range it can indicate that the motor or motor controller is malfunctioning. A non-limiting example of a malfunction that can be identified by the idle current of the pump motor is a malfunction in a stepper motor controller.

Data representing the deadband current and/or position of a pump motor can also be collected and used to detect malfunctions in the pump motor. In some embodiments of the present disclosure, it can be assumed that a speed control signal within the deadband should result in no current or positional changes. If a change occurs (outside of noise), then the motor (e.g., a stepper motor used in a peristaltic pump as part of a pump assembly 120) can be considered malfunctioning.

In some embodiments of the present disclosure, data about the software configuration of the generator 102 and/or pump assembly 120 are collected and used to determine whether one or more pump motors are malfunctioning. This data about the software configuration can include the firmware version of the generator 102 or controller 101, and the generator 102 and/or pump assembly 120 can switch or modify the mode of operation based on the software configuration information.

In some embodiments of the present disclosure, the pump data includes status information from the motor controller(s). The present disclosure contemplates that commercially available motor controllers can be used in some embodiments of the present disclosure. These motor controllers can include diagnostic and self-test capabilities. These capabilities can be used can be used in combination with embodiments of the present disclosure. In some embodiments of the present disclosure, the generator 102 can be configured to adjust the energy output of the radiofrequency ablation probe assembly 106 in response to a fault detected by a motor controller. As a non-limiting example, the generator 102 can reduce the radiofrequency energy output in response to receiving a fault from a stepper motor in the pump. This can allow the system to continue operating despite a fault in the stepper motor. In some embodiments of the present disclosure, the generator 102 can be disabled if the fault information from the stepper motor indicates that the motor has failed completely or will be unable to provide a sufficient flow of cooling fluid to the probe system 200 associated with the pump head 121.

Additionally, in some embodiments of the present disclosure, the pump data can be used as part of a diagnostic to determine whether the pump motor is programmed and configured correctly. Again, in some embodiments of the present disclosure, the parameters of a pump control loop can be adjusted based on the diagnostic information indicating that the pump motor is malfunctioning.

In some embodiments of the present disclosure, the pump data includes parameter values related to the performance characteristics of one or more motor controllers or motors. These parameter values can include speed control parameters (initial velocity, max velocity, acceleration, etc.). The speed control parameters can be stored in the motor controller. In some embodiments of the present disclosure, the programmable controller associated with the generator 102 can verify if the speed control parameters in the motor controller are correct and notify a user if the values are incorrect. According to some embodiments of the present disclosure, the controller 101 can determine whether the speed control parameters are correct for each motor controller corresponding to each pump head 121. The controller 101 can then disable the motor controllers that include incorrect speed control parameters. The controller 101 can generate an alert to the user that indicates which motor controllers include incorrect speed control parameters. The controller 101 can also generate an alert to the user indicating that the pump heads 121 corresponding to the disabled motor controllers are inactive, and instructing the user to use different pump heads 121 (for example when only two probes are needed, but the pump assembly 120 has four pump heads 121, the user can use the best performing two pump heads 121 and the generator 102 can disable the pump heads 121 with the worst performance).

In some embodiments of the present disclosure, the pump data includes flow rate data. The controller 101 can store a predetermined minimum flow rate threshold, and compare that minimum flow rate threshold to the flow rate through the pump heads 121. If the flow rate is below the minimum flow rate threshold, then the controller 101 can trip an alarm.

In some embodiments of the present disclosure, the pump data includes back pressure data. The controller 101 can use the back pressure data to sense what is connected to the pump. The controller 101 can store profiles representing different configurations of pump heads 121, probe assemblies 106, probe lengths, and configurations. The controller 101 can compare the stored profiles to the back pressure data, or to back pressure data combined with other pump data, to determine what configuration of probe assemblies 106 is attached to the device. As a non-limiting example, the controller 101 may associate a higher pressure with a longer (e.g., 150 mm) probe assembly 106 or associate a higher pressure with probe assemblies 106 that are "daisy chained" (i.e., connected so that fluid flows through multiple probe assemblies 106 before returning to the pump head 121).

In some embodiments of the present disclosure, the pump data includes the acceleration of the pump head 121. In some embodiments of the present disclosure, the motor controller includes a setting that controls the acceleration of the motor. In some embodiments of the present disclosure, the controller 101 can compare a measured value of pump head acceleration to the value of pump head acceleration stored in the motor controller. If the measured value is different than the value stored in the pump head controller (e.g., the difference between the two is greater than a specified threshold) then the controller 101 can trip an alarm indicating that the motor controller is malfunctioning.

In some embodiments of the present disclosure, the pump data includes change in current data. The change in current data can represent a measured difference in current draw between different pump speeds. The controller 101 can store a motor profile that shows the predicted current draw of the motor at different speeds. The controller 101 can compare the measured current change to the expected change based on the profile. If the change is different than the expected range, the controller 101 can determine that the pump may be improperly loaded or malfunctioning.

As described above, it is contemplated that any or all of the different types of pump data can be used in combination. As a non-limiting example, the change in current data can be combined with back pressure data to detect the load on the pump. Other combinations of pump data will become apparent to one of skill in the art.

The present disclosure contemplates that different parameters associated with the rotation of the pump head 121 can be measured and recorded by the controller 101 and that these parameters can be used to control the pump heads 121 and detect when a pump malfunctions. Non-limiting examples of these parameters include rotational position, RPM, torque, rotation speed and acceleration.

The present disclosure also contemplates that the pump data can include different parameters associated with the power provided to the pump assembly 120 can be measured and recorded by the controller 101, and that these parameters can be used to control the pump heads 121 and detect when a pump malfunctions. Non-limiting examples of these parameters include parameters associated with current and/or change in current provided to the pump assembly 120. These parameters associated with current and/or charge can be voltages, currents, changes in voltage, changes in current, or measures of instantaneous or total power (e.g., watts or joules). It should be understood that the parameters associated with the power provided to the pump assembly 120 can include parameters for each of the motors in the pump assembly 120. For example, in a quad pump unit, the parameters associated with the power provided to the pump assembly 120 can include a voltage, current, change in voltage, change in current, or any other parameter for each of the four pump heads 121 in the quad pump unit.

In some embodiments of the present disclosure, the controller 101 can determine whether the pump assembly 120 is operating properly comprises comparing the sensed parameters to corresponding predetermined parameters associated with proper operation. The present disclosure contemplates that the controller 101 can use any combination of parameters associated with power provided to the pump assembly 120 and parameters associated with the rotation of the pump head 121 to control the pump head 121 and determine whether the pump assembly 120 is operating properly. As a non-limiting example, in some embodiments of the present disclosure, the controller 101 can determine that the pump is not operating properly based on a current value and a torque value.

Some embodiments of the present disclosure can include a user interface, which can be displayed via display screen 103. The user interface can be configured to receive input. In some embodiments of the present disclosure, the user interface can receive an input from the user to control the pump assembly 120 test, and indicate, to the user, at least one of the one or more of the sensed parameters associated with the pump operation parameters. In some embodiments, the user interface is a graphical user interface. The graphical user interface can be configured to display a visual representation of the sensed parameters associated with the pump operation parameters and/or an alert. Example graphical user interfaces as shown in FIGS. 7-10, described in greater detail below.

Some embodiments of the present disclosure can also include a sensed output component that is configured to output, to a log, the sensed pump operation parameters for diagnostics and/or troubleshooting. As a non-limiting example, the log can be a file located on a computing device (e.g., the computing device shown in FIG. 6). The log can also be a paper log, for example a paper log printed by a printer (not shown) in response to receiving the output from the sensed output component.

FIG. 5A illustrates a method 500 for operating one or more pump heads 121 of the pump assembly 120. As show in FIG. 5A, pump operation parameters are received 502 from one or more pump function sensors. As described herein, the pump operation parameters can include data corresponding to any of the operation parameters associated with the pumps and/or pump motors. Based on the one or more pump operation parameters, the system can determine 504 whether the pump is operating correctly. The determination 504 can be made by the controller 101 and/or generator 102. Determining 504 whether the pump is operating correctly can be performed by comparing the operation parameters to predetermined pump operation parameters. The predetermined pump operation parameters can be stored in memory associated with the one or more computing devices 600, controllers 101, and/or generator 102. The pump operation parameters can be input into the memory using the graphical user interface or transmitted to the device using a network interface unit 600.

The generator 102, controller 101 and/or user interface can output an indication of whether the pump is operating correctly based on the determination 504. The indication can be a visual indication (e.g., an icon or light), an audio tone, or any other suitable indication. The indication can also be recorded and stored, or transmitted to another device (e.g., using WiFi or Bluetooth technology).

Based the determination 504 of whether the pump is operating correctly, the generator 102 can adjust 508 the operation of one or more pumps. This can include adjusting 508 the operation of at least one of the motor, pump head 121, or the power provided to the pump assembly 120. The pump function sensors can measure the change in the pump function parameters during and/or after the operation is adjusted 508 and determine whether the pump is operating correctly after the adjustment. The system can then repeat the steps of receiving 502 pump operation parameters, determining 504 whether the pump is operating correctly, outputting 506 an indication of whether the pump assembly 120 is operating properly, and adjusting operation 508 based on the pump operation parameters. These steps 502, 504, 506, 508 can be formed repeatedly, or as part of a closed loop control system for tuning the operation of the pump assembly 120. These steps 502, 504, 506, 508 can also be performed during treatment of a subject in order to validate whether the treatment is being correctly performed. The generator 102 and/or controller 101 can include different profiles of correct pump data corresponding to different numbers of probe assemblies 106, different types of pump assemblies 120, different types of probe assemblies 106, and different treatment procedures.

Some embodiments of the present disclosure include methods for implementing a pump self-test. The pump self-test can include identifying the generator 102 connected to the pump assembly 120. Non-limiting methods of identifying the generator 102 include using resistor ID, device ID stored in memory located on the pump, a secure network connection (e.g., SSL, Bluetooth, WiFi), serial communication signal (e.g., I2C, Serial/RS232). As discussed above, it is contemplated by the present disclosure that the pump assembly 120 can include one or more controllers, and that these controllers can include motor controllers. The pump assembly 120 can also include a pump assembly controller (not shown) which can include one or more components of the computer 600 (FIG. 6) with a processor 602, memory 604, and network interface 610. The network interface 610 can, as a not limiting example, be configured to communicate with the generator 102 or the controller 101 that is part of the generator 102 in order to provide information about the pump assembly 120 to the generator 102. This information can include information about the motors and motor controllers that are part of the pump assembly 120 such as the configuration of the stepper motors in the pump assembly 120. Non limiting examples of stepper motor configuration information include the firmware version of the stepper motor controllers, status of the stepper motor controllers, and parameter values of the stepper motor controllers. The parameter values can include any information related to the characteristics of the pump motors or pump motor controllers. Non-limiting examples of parameter values include initial velocity, maximum velocity, and acceleration, but other parameter values are contemplated by the present disclosure and described herein.

Based on the identity of the pump assembly 120, the generator 102 can determine compatible modes of operation. As a non-limiting example, the generator 102 can determine that only certain modes of operation are possible based on the capabilities of the generator 102 and pump assembly 120. The information about the compatible modes of operation can be provided to the user by means of the user interface, or by a network interface.

Some embodiments of the present disclosure include a "pump self-test" functionality. The generator 102 or controller 101 can initiate the pump self-test based on, for example, a user input, or as part of a programmed routine for treatment. In some embodiments of the present disclosure, the self-test includes the generator 102 supplying a power signal to the pump assembly 120 (e.g., a 24 volt power signal) and then the generator 102 measuring the idle current and position of the pump head 121 or heads 121. A non-limiting example of a position sensor that can be used in embodiments of the present disclosure is an encoder. The generator 102 can also provide a pump speed voltage to the pump assembly 120 that is within a predetermined deadband voltage. The deadband voltage corresponds to a voltage at which it is predicted that the pump heads 121 should not turn. The generator 102 can measure the current and position of the pump head 121 while the voltage is applied. In some embodiments of the present disclosure some or all of the measured values of the idle current, deadband current, firmware version, status, parameter values, etc. are compared to predetermined acceptable values. Based on the difference between the acceptable values and measured values, one or more alarms can be tripped by the generator 102, and the values themselves and/or warnings based on those values can be displayed using the user interface. The generator 102 and/or controller 101 can also disable pump heads 121 corresponding to motors with parameter values that are out of range according to predetermined criteria.

Some embodiments of the present disclosure can perform a "loaded pump test". The generator 102 or controller 101 can initiate the loaded pump test based on, for example, a user input, or as part of a programmed routine for treatment. In some embodiments of the present disclosure, the self-test includes the generator 102 supplying a power signal to the pump assembly 120 (e.g., a 24 volt power signal) and then the generator 102 measuring the idle current and position of the pump head 121 or heads 121 (e.g., by an encoder). The generator 102 can supply a voltage that is above the deadband voltage. In some embodiments of the present disclosure, the voltage applied by the generator 102 is only slightly greater than the deadband voltage so that the pump heads 121 slowly turn. The generator 102 can then record the current and position of the pump head or heads 121 as they turn. Based on the parameter values recorded by the pump function sensors, the generator 102 or controller 101 can determine torque (e.g., from current), rotational speed (e.g., from position over time), flow rate (e.g., from speed), and/or back pressure (e.g., based on flow rate and torque). Like the pump self-test, the parameter values can be compared to predetermined "acceptable" parameter values to determine whether a pump head 121 is operating correctly, the "status" of the pump head 121. The generator 102 can then increase the pump speed voltage applied by a predetermined increment (e.g., 0.5V) and measure the parameter values using the pump function sensors after the voltage has been increased. Again, based on the data from the pump function sensor, the generator 102 or controller 101 can determine torque (e.g., from current), rotational speed (e.g., from position over time), flow rate (e.g., from speed), and/or back pressure (e.g., based on flow rate and torque). In some embodiments of the present disclosure, the pump speed voltage applied by the generator 102 can be repeatedly increased until the pump reaches a predetermined maximum speed. The parameter values recorded at each voltage level can be stored, and used by the generator 102 and/or controller 101 to characterize the performance of the pump heads 121. The performance of the pump heads 121 can be compared to a known performance profile to determine whether any of the pump heads 121 is improperly configured, malfunctioning, or otherwise not capable of performing a procedure (e.g., the procedure selected by the user). Information from the loaded self-test can be stored in the controller 101, generator 102, and/or displayed via display screen 103.

Figure 5B:
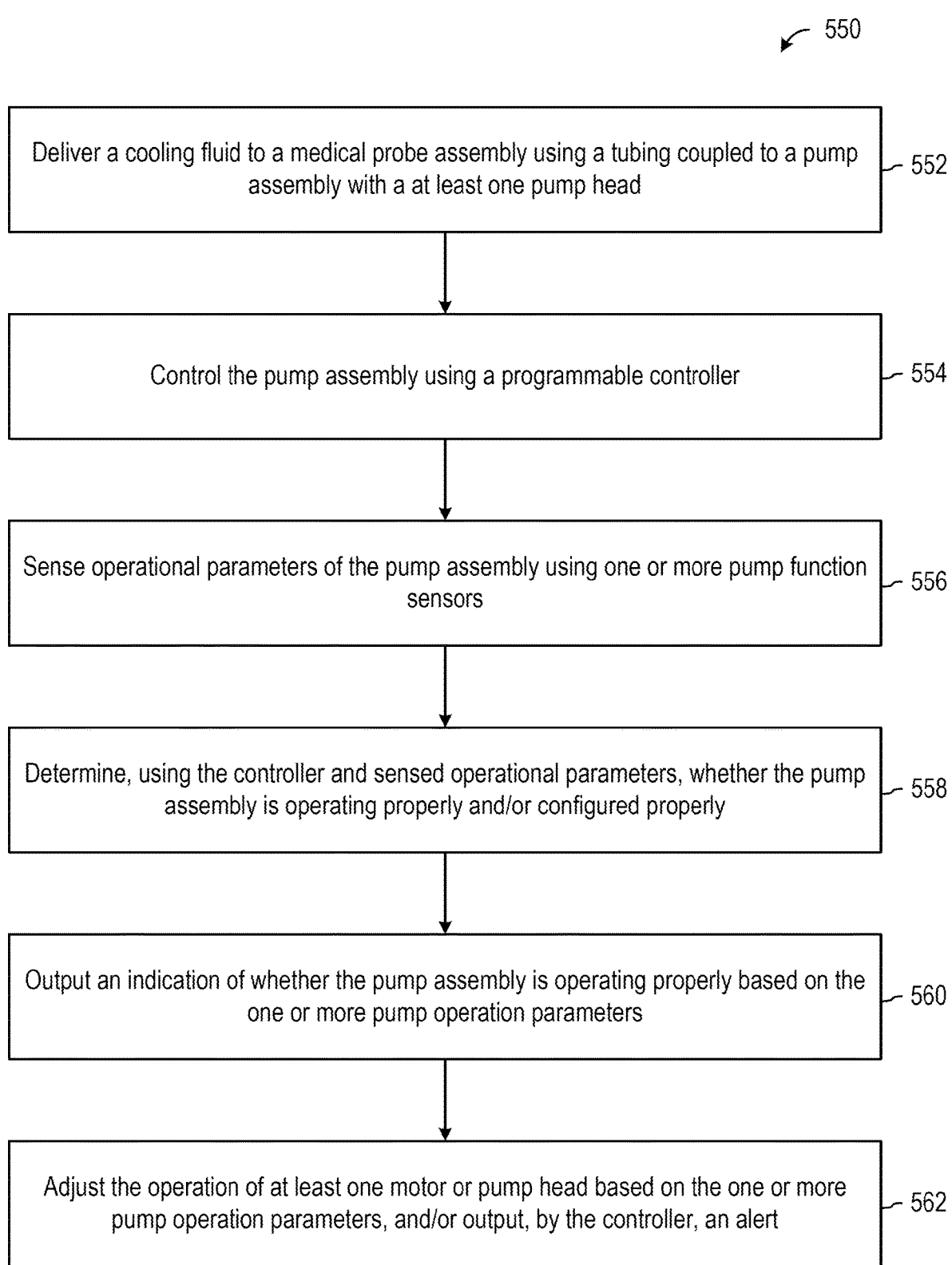
FIG. 5B is a flow chart of a method for performing a loaded pump test, according to some embodiments.

FIG. 5B illustrates a method 550 for testing a pump assembly 120 for a cooled radiofrequency (RF) treatment procedure, according to an embodiment of the present disclosure. The method 550 shown in FIG. 5B can be used to implement a loaded self-test. For example, the pump assembly 120 and/or system can be the pump assembly 120 shown in FIGS. 1-4. The method 550 can include delivering 552, by tubing coupled to at least a pump assembly 120 a cooling fluid to a medical probe assembly, for the cooled RF treatment procedure. As described above with reference to FIGS. 1-4, the pump assembly 120 can include any number of pump heads 121 and can be configured to operate with different numbers of probe assemblies 106 connected to those pump heads 121. Also as described above, the pump assembly can include one or more motors for driving the pump heads.

Figure 6:
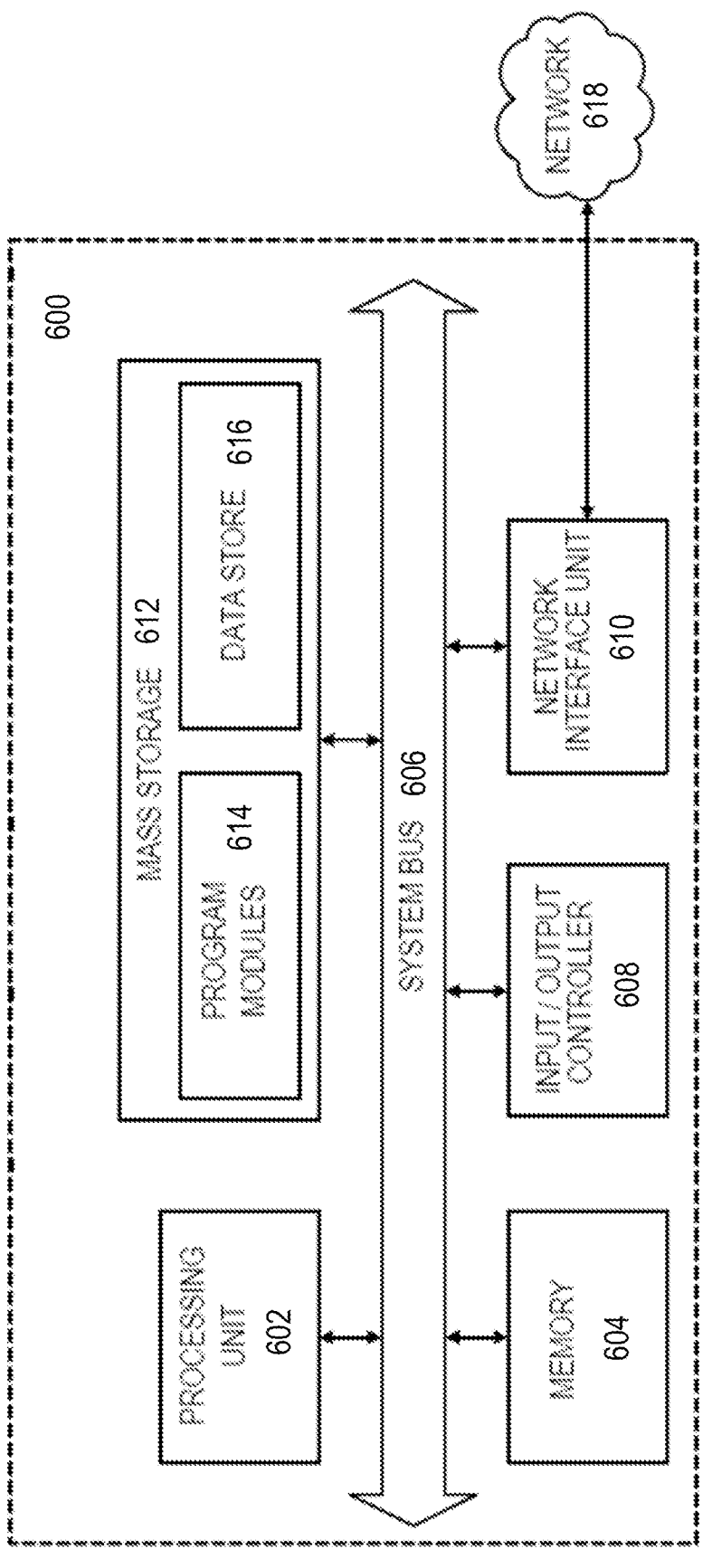
FIG. 6 is a block diagram of a computer device capable of implementing various methods described herein, according to some embodiments.

The functions of the pump assembly 120 can be controlled 554 using a programmable controller operably connected to the pump assembly. The controller 554 can include one or more components of the example computer 600 as shown in FIG. 6. Operation parameters of the pump assembly 120 can be sensed 556 by one or pump function sensors, operation parameters associated with the pump assembly 120 and communicating the pump operation parameters to the controller. The pump operation parameters can indicate whether the pump assembly 120 is operating properly, and the pump operation parameters can include an indication, from the one or more pump function sensors of at least one parameter associated with the rotation of the pump head 121 or at least one parameter associated with power provided to the pump assembly 120.

The method 550 can include determining 558 by the controller and based on the sensed pump operation parameters, whether the pump assembly 120 is operating properly and/or is configured properly and outputting 560 an indication, for display via display screen 103, at least one of the pump operation parameters. Alternatively, or additionally, the controller can output 560 an alert. Again, as described above, the alert can be output 560 or displayed using a user interface (e.g., via display screen 103).

Based on whether the pump assembly 120 is operating properly and/or is configured properly, the controller can adjust 562 the operation of at least one of the at least one respective motor, at least one pump head 121, or the power provided to the pump assembly 120, such that the pump assembly 120 operates properly and such that the cooling system is a closed loop feedback system.

The method 550 described herein can be used with embodiments of the systems disclosed by the present disclosure. As described above, non-limiting examples of the types of sensors that can be used for the one or more pump function sensors include torque sensors, rotary encoders, acceleration sensors, and sensors to detect current or a non-invasive fluid flow sensors. The use of other suitable sensors, including other sensors disclosed throughout the present disclosures, is contemplated. Another non-limiting example of a pump operation parameter that can be sensed 556 is the flow rate of the pump.

As described above, a parameter associated with the rotation of the pump head 121 can include at least one of rotational position, RPM, torque, rotation speed, or acceleration. Again, these are intended only as non-limiting examples of parameters contemplated by the present disclosure and it should be understood that other parameters can be used.

Similarly, parameters associated with power provided to the pump assembly 120 can be used by the method 550 to determine 558 whether the pump assembly 120 is operating or configured correctly, output 560 an indication, and/or adjust 562 the operation of the pump assembly. The parameters associated with the power can include a parameter associated with the electrical current provided to the pump assembly. The parameters associated with the power provided to the pump assembly 120 can also include the temperature of the at least one respective motor. Again, the present disclosure contemplates that these parameters can be used alone or in combination in different embodiments of the present disclosure to perform the steps of determining 558, outputting 560 and/or adjusting 562.

As described above, adjusting 562 the operation of the motor and/or pump head 121 can be done as part of a closed loop control system configured to control and/or optimize one or more parameters. In some embodiments of the present disclosure, the method can also include determining 558, by the controller, whether the pump assembly 120 is operating properly and/or is configured properly can include comparing the sensed pump operation parameters to corresponding predetermined parameters associated with proper operation.

In some embodiments of the present disclosure, the method can also include sensing 556, one or more parameters associated with flow rate of the cooling fluid. Sensing 556 the one or more pump function sensors can include receiving data from one or more sensors. Non-limiting examples of the sensors include flow rate sensors and back pressure sensors. In some embodiments of the present disclosure, sensing 556 can also include measuring one or more parameters associated with flow rate of the cooling fluid using one or more pump function sensors.

In some embodiments of the present disclosure, the method 550 can also include receiving user input that is associated with the pump assembly 120 test and providing the user input to the controller. The user input can be received through a user interface. It is also contemplated by the present disclosure that the method 550 can include outputting one or more of the sensed parameters associated with the pump operation parameters for display. The display can include a visual representation of the sensed parameters associated with the pump operation parameters or the alert. As described above, outputting 550 can also include outputting 550 to a log. The log can include information related to the sensed pump operation parameters for diagnostics and/or troubleshooting. Again, as described above, as a non-limiting example, the log can be a file located on a computing device (e.g., the computing device shown in FIG. 6). The log can also be a paper log, for example a paper log printed by a printer (not shown) in response to receiving the output from the sensed output component.

FIG. 6 is a computer architecture diagram showing a general computing system capable of implementing one or more embodiments of the present disclosure described herein. A computer 600 may be configured to perform one or more functions associated with embodiments illustrated in one or more of FIGS. 1-5. The controller 101 and generator 102 can include one or more components of the computer 600. It should be appreciated that the computer 600 may be implemented within a single computing device or a computing system formed with multiple connected computing devices. For example, the computer 600 may be configured for a server computer, desktop computer, laptop computer, or mobile computing device such as a smartphone or tablet computer, or the computer 600 may be configured to perform various distributed computing tasks, which may distribute processing and/or storage resources among the multiple devices.

As shown, the computer 600 includes a processing unit 602, a system memory 604, and a system bus 606 that couples the memory 604 to the processing unit 602. The computer 600 further includes a mass storage device 612 for storing program modules. The program modules 614 may include modules executable to perform one or more functions associated with embodiments illustrated in one or more of FIGS. 1-5. The mass storage device 612 further includes a data store 616.

The mass storage device 612 is connected to the processing unit 602 through a mass storage controller (not shown) connected to the bus 606. The mass storage device 612 and its associated computer storage media provide non-volatile storage for the computer 600. By way of example, and not limitation, computer-readable storage media (also referred to herein as "computer-readable storage medium" or "computer-storage media" or "computer-storage medium") may include volatile and non-volatile, removable and non-removable media implemented in any method or technology for storage of information such as computer-storage instructions, data structures, program modules, or other data. For example, computer-readable storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 600. Computer-readable storage media as described herein does not include transitory signals.

According to various embodiments, the computer 600 may operate in a networked environment using connections to other local or remote computers through a network 618 via a network interface unit 610 connected to the bus 606. The network interface unit 610 may facilitate connection of the computing device inputs and outputs to one or more suitable networks and/or connections such as a local area network (LAN), a wide area network (WAN), the Internet, a cellular network, a radio frequency network, a Bluetooth-enabled network, a Wi-Fi enabled network, a satellite-based network, or other wired and/or wireless networks for communication with external devices and/or systems.

The computer 600 may also include an input/output controller 608 for receiving and processing input from a number of input devices. Input devices may include, but are not limited to, keyboards, mice, stylus, touchscreens, microphones, audio capturing devices, or image/video capturing devices. An end user may utilize such input devices to interact with a user interface, for example a graphical user interface on one or more display devices (e.g., computer screens), for managing various functions performed by the computer 600, and the input/output controller 608 may be configured to manage output to one or more display devices for visually representing data. In some embodiments, display screen 103 is one such display device that may be communicably coupled to computer 600 via input/output controller 608.

The bus 606 may enable the processing unit 602 to read code and/or data to/from the mass storage device 612 or other computer-storage media. The computer-storage media may represent apparatus in the form of storage elements that are implemented using any suitable technology, including but not limited to semiconductors, magnetic materials, optics, or the like. The program modules 614 may include software instructions that, when loaded into the processing unit 602 and executed, cause the computer 600 to provide functions associated with embodiments illustrated in FIGS. 1-5. The program modules 614 may also provide various tools or techniques by which the computer 600 may participate within the overall systems or operating environments using the components, flows, and data structures discussed throughout this description. In general, the program module 614 may, when loaded into the processing unit 602 and executed, transform the processing unit 602 and the overall computer 600 from a general-purpose computing system into a special-purpose computing system.

The processing unit 602 may be constructed from any number of transistors or other discrete circuit elements, which may individually or collectively assume any number of states. More specifically, the processing unit 602 may operate as a finite-state machine, in response to executable instructions contained within the program modules 614. These computer-executable instructions may transform the processing unit 602 by specifying how the processing unit 602 transitions between states, thereby transforming the transistors or other discrete hardware elements constituting the processing unit 602. Encoding the program modules 614 may also transform the physical structure of the computer-readable storage media. The specific transformation of physical structure may depend on various factors, in different implementations of this description. Examples of such factors may include but are not limited to: the technology used to implement the computer-readable storage media, whether the computer-readable storage media are characterized as primary or secondary storage, and the like. For example, if the computer-readable storage media are implemented as semiconductor-based memory, the program modules 614 may transform the physical state of the semiconductor memory, when the software is encoded therein. For example, the program modules 614 may transform the state of transistors, capacitors, or other discrete circuit elements constituting the semiconductor memory.

As another example, the computer-storage media may be implemented using magnetic or optical technology. In such implementations, the program modules 614 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present disclosure.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. The patentable scope of certain embodiments of the disclosed technology is indicated by the appended claims and claims to be filed in non-provisional patent application(s) claiming priority to the present application, rather than the foregoing description.

Figure 7:
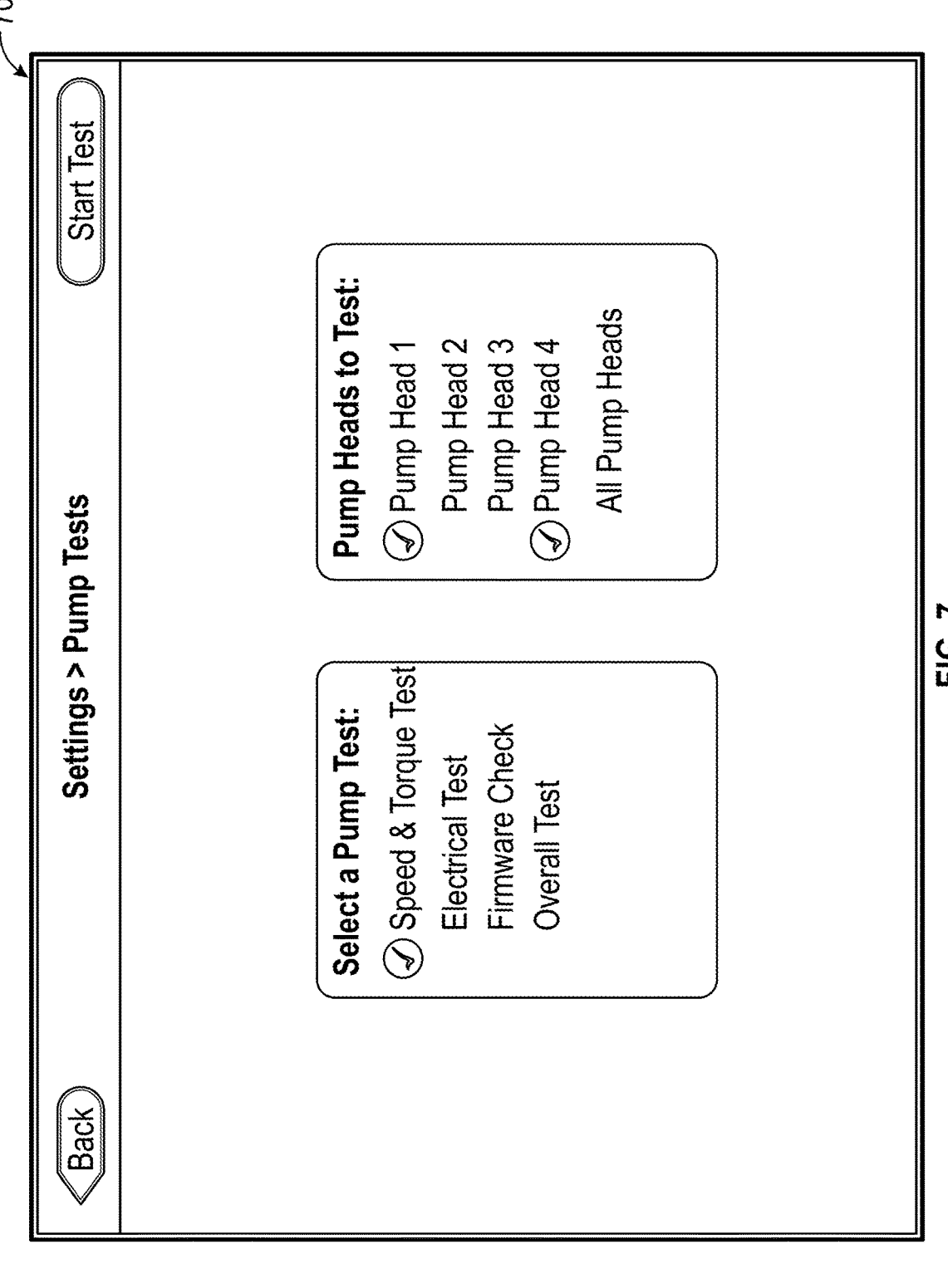
FIG. 7 is an example user interface for selecting a pump test, according to some embodiments.

Referring now to FIG. 7, an example user interface 700 for selecting a pump test is shown, according to some embodiments. In some embodiments, interface 700 is presented via display screen 103 or any other display device that can be coupled to generator 102—or, more particularly, controller 101. As shown, interface 700 may be used to select any of the pump tests described herein. In this example, the user may select one of a "speed & torque" test, an "electrical" test, a "firmware" check", or an overall system test. Further, interface 700 allows a user to select one or more pump heads to be tested. For example, the user may choose one or more individual pump heads, or may choose to test all pump heads. Once the parameters for the test are entered, the user may select a "start test" button or icon to begin the test, as in the methods described above.

Figure 9:
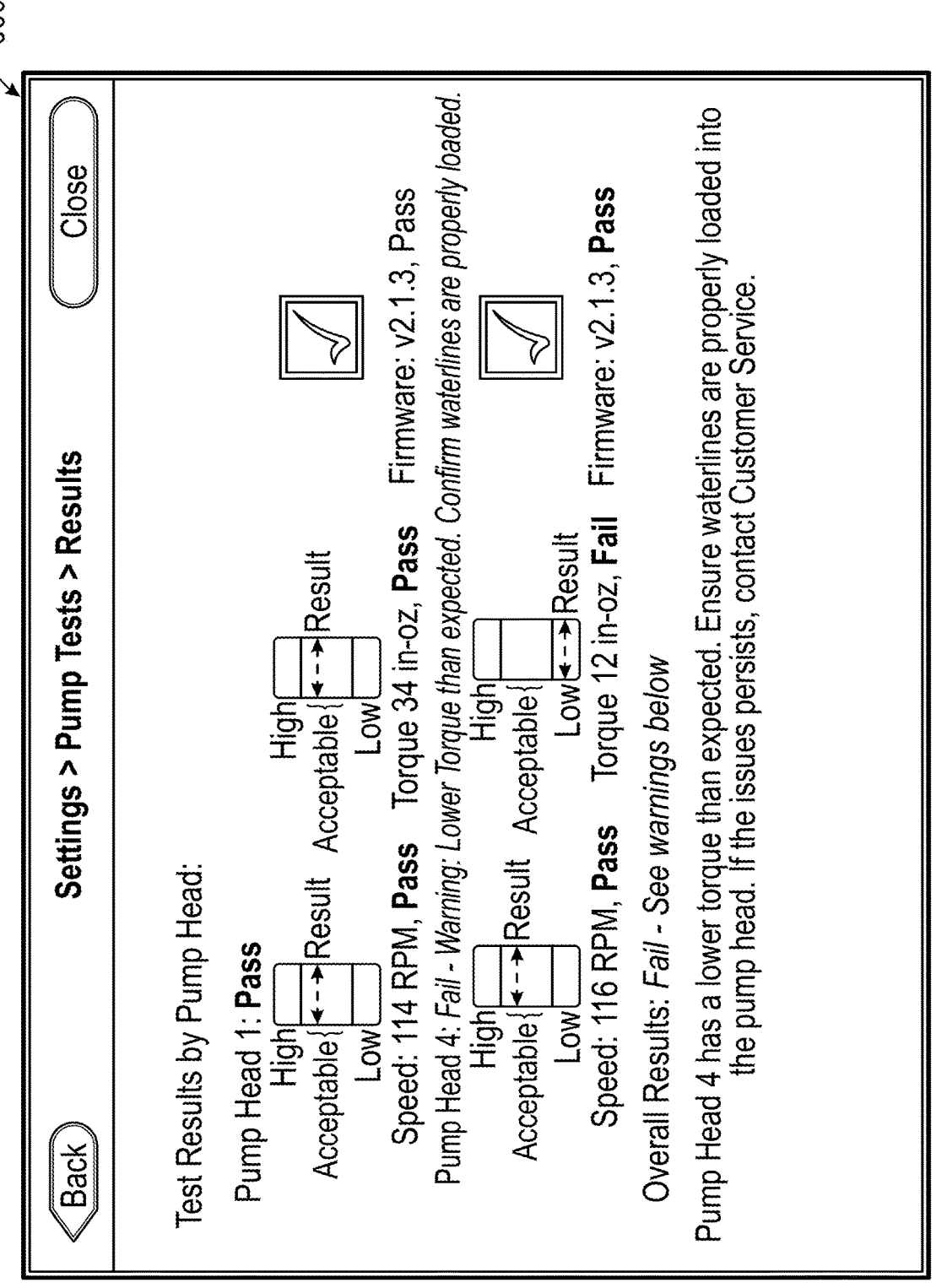

Referring now to FIGS. 8 and 9, example user interfaces for reviewing the results of a pump test are shown, according to some embodiments. In some embodiments, interfaces 800 and 900 are presented via display screen 103 or any other display device that can be coupled to generator 102—or, more particularly, controller 101. FIG. 8, in particular, shows an example user interface 800 which includes text-based test results. In some embodiments, interface 800 may be presented (e.g., via display screen 103) upon completion of one or more tests (e.g., as selected via interface 700). In this example, 'Pump Head 1' and 'Pump Head 4' were tested. As shown, 'Pump Head 4' failed the firmware check because "Pump Head 4 has the incorrect firmware installed." FIG. 9 shows an example user interface 900 in which the test results are shown graphically. In this example, the test results (e.g., from interface 800) are shown as graphics or icons, in addition to being provided as text. For example, the speed test results are shown as graphs indicating a range of speeds, and an "acceptable" value zone.

Figure 10:
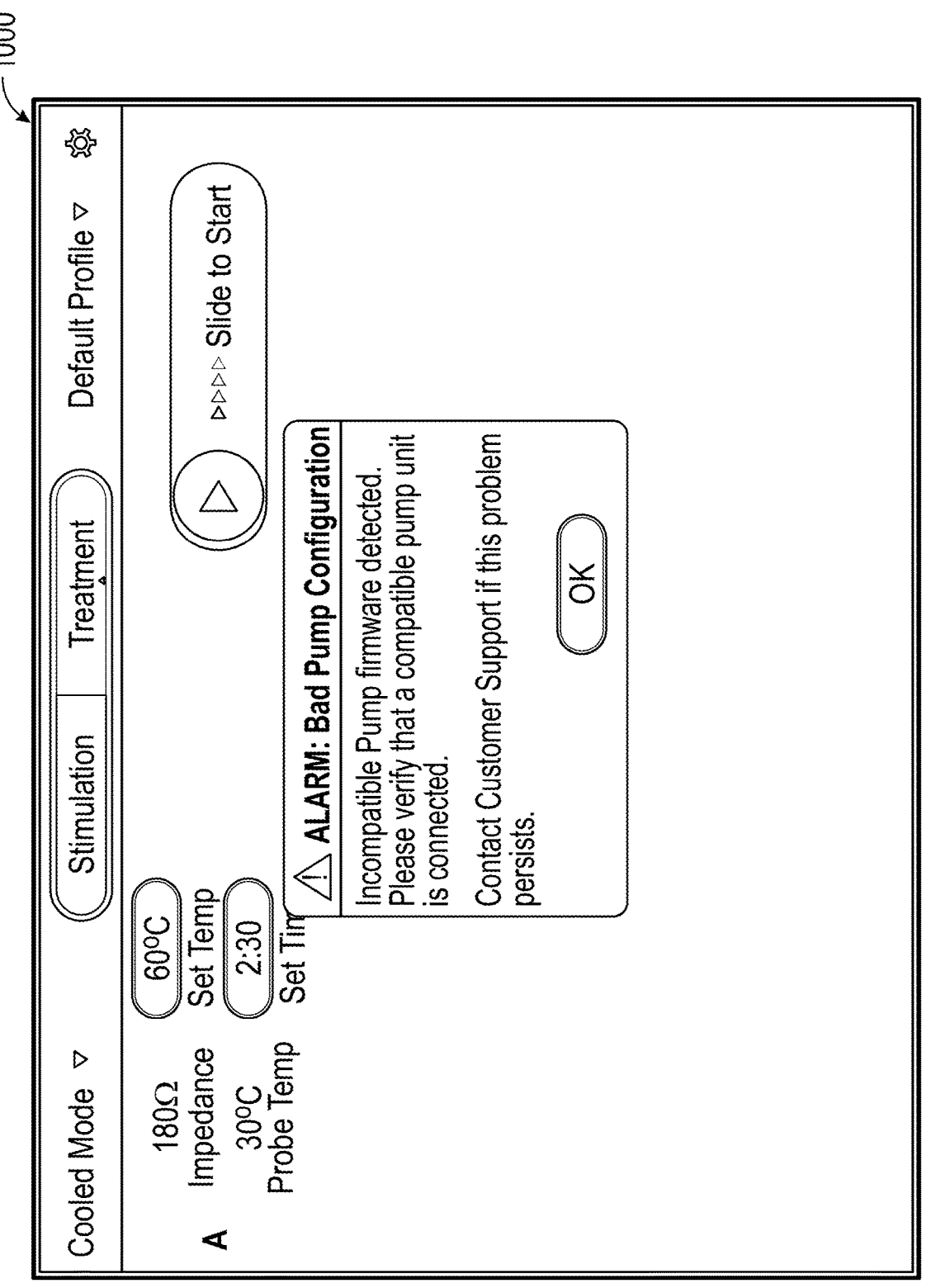
FIG. 10 is an example user interface of a pump configuration alarm, according to some embodiments.

Referring now to FIG. 10, an example user interface 1000 of a pump configuration alarm is shown, according to some embodiments. In some embodiments, interface 1000 is presented via display screen 103 or any other display device that can be coupled to generator 102—or, more particularly, controller 101. As described above, alerts may be generated and displayed whenever an issue or fault is detected, or when one or more parameters of the pump heads 121 are outside of an acceptable range or do not meet a required value (e.g., when one or more of pump heads 121 fail a test). In some embodiments, interface 1000 may be displayed as an overlay to any other user interfaces shown on display screen 103. In this example, interface 1000 overlays a standard control screen for controlling probes assemblies 106 during a procedure. In this example, interface 1000 displays an alarm for "Bad Pump Configuration" because the firmware of a pump is out of date or incompatible.

What is claimed is:

1. A system for testing a pump assembly for a cooled radiofrequency (RF) treatment procedure, the system comprising:

a pump assembly and at least one pump head driven by at least one respective motor, wherein the at least one pump head is coupled to tubing for delivering a cooling fluid to a medical probe assembly, and wherein the at least one pump head is configured to pump the cooling fluid through the tubing for the cooled RF treatment procedure;

a plurality of pump function sensors for sensing operation parameters associated with the pump assembly, wherein the pump operation parameters indicate whether the pump assembly is operating properly, and wherein the pump operation parameters include an indication of at least one parameter associated with the rotation of the at least one pump head and at least one parameter associated with power provided to the pump assembly;

a generator operatively coupled to the pump assembly; and a controller in communication with the pump assembly and the plurality of pump function sensors, the controller configured to:

determine, based at least in part on back pressure data obtained via the at least one pump head and a plurality of stored configuration profiles, a configuration of the medical probe assembly;

determine one or more generator characteristics, wherein the generator determines one or more available modes of operation based on the configuration of the medical probe assembly and the one or more generator characteristics;

determine a plurality of parameter values based, at least in part, on the configuration of the medical probe assembly and the one or more generator characteristics;

determine, based on the sensed pump operation parameters, whether the pump assembly is operating properly and/or is configured properly by comparing the sensed pump operation parameters to the determined plurality of parameter values; and at least one of:

output an indication, for display, of at least one of the pump operation parameters; or responsive to determining that the pump assembly is not operating properly and/or is not configured properly, at least one of: i) adjust operation of at least one of the at least one respective motor, at least one pump head, or the power provided to the pump assembly, such that the pump assembly operates properly; or ii) output an alert.

2. The system of claim 1, wherein the plurality of pump function sensors include one or more of a torque sensor, a rotary encoder, an acceleration sensor, or a current sensor.

3. The system of claim 1, wherein the plurality of pump function sensors include a non-invasive fluid flow sensor.

4. The system of claim 1, wherein the pump operation parameters include flow rate.

5. The system of claim 1, wherein the at least one parameter associated with the rotation of the at least one pump head includes at least one of rotational position, revolutions per minute (RPM), torque, rotation speed, or acceleration.

6. The system of claim 1, wherein the at least one parameter associated with power provided to the pump assembly includes a parameter associated with current provided to the pump assembly.

7. The system of claim 1, wherein the at least one parameter associated with power provided to the pump assembly includes a temperature of the at least one respective motor.

8. The system of claim 1, wherein the plurality of pump function sensors further include at least one of a flow rate sensor or a back pressure sensor, configured to sense one or more parameters associated with flow rate of the cooling fluid.

9. The system of claim 1, wherein the pump assembly is a peristaltic pump assembly.

10. The system of claim 1, wherein the system further comprises a sensed output component that is configured to output, to a log, the sensed pump operation parameters for diagnostics and/or troubleshooting.

11. The system of claim 1, further comprising a user interface configured to receive user input that is associated with the pump assembly test, wherein the user interface is configured to provide the user input to the controller.

12. The system of claim 1, further comprising a user interface, wherein the user interface is configured to output, for display, at least one of the sensed parameters associated with the pump operation parameters.

13. The system of claim 1, further comprising a graphical user interface, wherein the graphical user interface is configured to display, to a user, at least one visual representation of the sensed parameters associated with the pump operation parameters or the alert.

14. A method for testing a pump assembly for a cooled radiofrequency (RF) treatment procedure, comprising:

delivering, by tubing coupled to at least one pump assembly including at least one pump head for driving the at least one pump head, a cooling fluid to a medical probe assembly, for the cooled RF treatment procedure, wherein the at least one pump assembly is operatively coupled to a generator;

controlling, by a controller operatively connected to the at least one pump assembly, functions of the pump assembly;

sensing, by a plurality of pump function sensors, operation parameters associated with the at least one pump assembly; and communicating the pump operation parameters to the controller, wherein the pump operation parameters indicate whether the at least one pump assembly is operating properly, and wherein the pump operation parameters include an indication, from the plurality of pump function sensors, of at least one parameter associated with the rotation of the at least one pump head and at least one parameter associated with power provided to the at least one pump assembly;

determining, by the controller and based on back pressure data obtained via the at least one pump head and a plurality of stored configuration profiles, a configuration of the medical probe assembly;

determining, by the controller, one or more generator characteristics, wherein the generator determines one or more available modes of operation based on the configuration of the medical probe assembly and the one or more generator characteristics;

determining, by the controller, a plurality of parameter values based, at least in part, on the configuration of the medical probe assembly and the one or more generator characteristics;

determining, by the controller and based on the sensed pump operation parameters, whether the at least one pump assembly is operating properly and/or is configured properly by comparing the sensed pump operation parameters to the determined plurality of parameter values; and at least one of:

outputting, by the controller, an indication, for display, at least one of the pump operation parameters; or responsive to determining, by the controller, that the at least one pump assembly is not operating properly and/or is not configured properly, performing at least one of: i) adjusting, by the controller, operation of at least one respective motor, the at least one pump head, or the power provided to the at least one pump assembly, such that the at least one pump assembly operates properly; or ii) outputting, by the controller, an alert.

15. The method of claim 14, wherein the plurality of pump function sensors include one or more of a torque sensor, rotary encoder, acceleration sensor, or sensor to detect current.

16. The method of claim 14, wherein the plurality of pump function sensors include a non-invasive fluid flow sensor.

17. The method of claim 14, wherein the pump operation parameters include flow rate.

18. The method of claim 14, wherein the at least one parameter associated with the rotation of the at least one pump head includes at least one of rotational position, RPM, torque, rotation speed or acceleration.

19. The method of claim 14, wherein the at least one parameter associated with power provided to the at least one pump assembly includes a parameter associated with current provided to the at least one pump assembly.

20. The method of claim 14, wherein the at least one parameter associated with power provided to the at least one pump assembly includes a temperature of the at least one respective motor.

21. The method of claim 14, comprising sensing, by the plurality of pump function sensors, one or more parameters associated with flow rate of the cooling fluid, wherein the plurality of pump function sensors include at least one of a flow rate sensor or a back pressure sensor.

22. The method of claim 14, comprising sensing, by the plurality of pump function sensors, one or more parameters associated with flow rate of the cooling fluid.

23. The method of claim 14, comprising outputting, to a log, the sensed pump operation parameters for diagnostics and/or troubleshooting.

24. The method of claim 14, further comprising receiving, by the controller and via a user interface, a user input that is associated with the pump assembly test, and wherein the user interface is configured to provide the user input to the controller.

25. The method of claim 14, further comprising outputting, by the controller and for display via a user interface, at least one of the sensed parameters associated with the pump operation parameters.

26. The method of claim 14, further comprising displaying, by the controller and for display via a user interface, at least one visual representation of the sensed parameters associated with the pump operation parameters or the alert.

* * * * *